US011160721B2

(12) United States Patent
Wersland et al.

(10) Patent No.: US 11,160,721 B2
(45) Date of Patent: Nov. 2, 2021

(54) PERCUSSIVE THERAPY DEVICE WITH VARIABLE AMPLITUDE

(71) Applicant: Theragun, Inc., Beverly Hills, CA (US)

(72) Inventors: Jason Wersland, Manhattan Beach, CA (US); Benjamin Nazarian, Beverly Hills, CA (US); Jaime Sanchez Solana, Los Angeles, CA (US); Eduardo Merino, Beverly Hills, CA (US); Richard Tang, Shenzhen (CN)

(73) Assignee: THERAGUN, INC., Beverly Hills, CA (US)

( * ) Notice: Subject to any disclaimer, the term of this patent is extended or adjusted under 35 U.S.C. 154(b) by 0 days.

(21) Appl. No.: 17/018,044

(22) Filed: Sep. 11, 2020

(65) Prior Publication Data

US 2020/0405574 A1    Dec. 31, 2020

Related U.S. Application Data

(63) Continuation-in-part of application No. 16/869,402, filed on May 7, 2020, now Pat. No. 10,857,064, (Continued)

(51) Int. Cl.
*A61H 23/00* (2006.01)
*A61H 1/00* (2006.01)
(Continued)

(52) U.S. Cl.
CPC ........... *A61H 23/006* (2013.01); *A61H 1/008* (2013.01); *A61H 15/0085* (2013.01);
(Continued)

(58) Field of Classification Search
CPC .. A61H 23/006; A61H 1/008; A61H 15/0085; A61H 23/00; A61H 23/0254;
(Continued)

(56) References Cited

U.S. PATENT DOCUMENTS 3,172,675 A    3/1965 Gonzalez
3,545,301 A    12/1970 Richter
(Continued)

FOREIGN PATENT DOCUMENTS

DE    3633888 A1 * 4/1988 ............ B23D 51/16
JP    1990019157    1/1990
(Continued)

OTHER PUBLICATIONS

PCT/US2016/038326 International Search Report & Written Opinion dated Sep. 1, 2016.
(Continued)

*Primary Examiner* — Timothy A Stanis
*Assistant Examiner* — Matthew R Moon
(74) *Attorney, Agent, or Firm* — Jeffer Mangels; Butler & Mitchell LLP; Brennan C. Swain, Esq.

(57) ABSTRACT

A percussive therapy device that includes a housing, an electrical source, a motor positioned in the housing, a switch for activating the motor, a push rod assembly operatively connected to the motor and configured to provide reciprocating motion in response to activation of the motor, and a massage attachment secured to a distal end of the push rod assembly. The reciprocating motion of the push rod assembly has a user-adjustable amplitude.

19 Claims, 16 Drawing Sheets

Related U.S. Application Data which is a continuation-in-part of application No. 16/675,772, filed on Nov. 6, 2019, now Pat. No. 10,702,448, which is a continuation-in-part of application No. 16/357,984, filed on Mar. 19, 2019, now Pat. No. 10,912,707, which is a continuation of application No. 15/920,322, filed on Mar. 13, 2018, now Pat. No. 10,357,425, which is a continuation-in-part of application No. 15/458,920, filed on Mar. 14, 2017, now abandoned, which is a continuation-in-part of application No. 15/186,859, filed on Jun. 20, 2016, now abandoned.

(60) Provisional application No. 62/182,525, filed on Jun. 20, 2015, provisional application No. 62/785,151, filed on Dec. 26, 2018, provisional application No. 62/844,424, filed on May 7, 2019, provisional application No. 62/899,098, filed on Sep. 11, 2019, provisional application No. 63/044,860, filed on Jun. 26, 2020, provisional application No. 63/065,114, filed on Aug. 13, 2020.

(51) Int. Cl.

| | | |
|---|---|---|
| *A61H 23/02* | (2006.01) | |
| *A61H 15/00* | (2006.01) | |
| *B27B 19/00* | (2006.01) | |
| *B23D 51/16* | (2006.01) | |
| *B23D 49/10* | (2006.01) | |
| *B23D 49/00* | (2006.01) | |
| *B27B 19/02* | (2006.01) | |
| *A61B 17/14* | (2006.01) | |

(52) U.S. Cl.
CPC ......... *A61H 23/00* (2013.01); *A61H 23/0254* (2013.01); *A61B 17/142* (2016.11); *A61H 2023/029* (2013.01); *A61H 2201/0165* (2013.01); *A61H 2201/12* (2013.01); *A61H 2201/123* (2013.01); *A61H 2201/1207* (2013.01); *A61H 2201/1215* (2013.01); *A61H 2201/14* (2013.01); *A61H 2201/149* (2013.01); *A61H 2201/1481* (2013.01); *A61H 2201/1664* (2013.01); *B23D 49/007* (2013.01); *B23D 49/10* (2013.01); *B23D 51/16* (2013.01); *B27B 19/00* (2013.01); *B27B 19/002* (2013.01); *B27B 19/02* (2013.01)

(58) Field of Classification Search
CPC ...... A61H 2023/029; A61H 2201/0165; A61H 2201/1664; A61H 2201/1481; A61H 2201/149; A61H 2201/12; A61H 2201/1207; A61H 2201/1215; A61H 2201/123; A61H 2201/14; B27B 19/02; B27B 19/00; B27B 19/002; B23D 49/10; B23D 51/16; B23D 49/007
USPC ........... 30/392, 393, 183, 189, 277; 81/9.22, 81/465, 57.39; 173/49, 114, 115, 201, 173/205, 29
See application file for complete search history.

(56) References Cited

U.S. PATENT DOCUMENTS

| | | | |
|---|---|---|---|
| 3,626,934 A | 12/1971 | Andis | |
| 3,942,251 A | 3/1976 | Griffies | |
| 4,031,763 A * | 6/1977 | Eisenberg | B23D 51/16 74/50 |
| 4,150,668 A | 4/1979 | Johnston | |
| 4,173,217 A | 11/1979 | Johnston | |
| 4,549,535 A | 10/1985 | Wing | |
| 4,566,442 A | 1/1986 | Mabuchi | |
| 4,730,605 A | 3/1988 | Noble et al. | |
| 5,085,207 A | 2/1992 | Fiore | |
| 5,212,887 A | 5/1993 | Farmerie | |
| 5,417,644 A | 5/1995 | Lee et al. | |
| 5,569,168 A | 10/1996 | Hartwig | |
| 5,573,500 A | 11/1996 | Katsunuma | |
| 5,951,501 A | 9/1999 | Griner | |
| 6,228,042 B1 | 5/2001 | Dungan | |
| 6,663,657 B1 | 12/2003 | Miller | |
| 6,682,496 B1 | 1/2004 | Pivaroff | |
| 7,927,259 B1 | 4/2011 | Rix | |
| 7,996,996 B2 | 8/2011 | Hirabayashi | |
| 8,342,187 B2 | 1/2013 | Kalman | |
| 8,951,216 B2 | 2/2015 | Yoo et al. | |
| 10,314,762 B1 | 6/2019 | Marton | |
| 2001/0016697 A1 | 8/2001 | Gorsen | |
| 2003/0009116 A1 | 1/2003 | Luettgen | |
| 2003/0094356 A1 | 5/2003 | Waldron | |
| 2003/0144615 A1 | 7/2003 | Lin | |
| 2003/0195443 A1 | 10/2003 | Miller | |
| 2005/0109137 A1* | 5/2005 | Hartmann | B23D 51/16 74/25 |
| 2006/0025710 A1 | 2/2006 | Schulz | |
| 2006/0123941 A1 | 6/2006 | Wadge | |
| 2006/0192527 A1 | 8/2006 | Kageler | |
| 2007/0144310 A1 | 6/2007 | Pozgay | |
| 2007/0150004 A1 | 6/2007 | Colloca | |
| 2007/0270727 A1 | 11/2007 | Khorassani Zadeh | |
| 2008/0103419 A1 | 5/2008 | Adamson | |
| 2008/0169715 A1* | 7/2008 | Mills | B06B 1/162 310/81 |
| 2008/0200849 A1 | 8/2008 | Hollington | |
| 2012/0253245 A1 | 10/2012 | Stanbridge | |
| 2013/0133210 A1 | 5/2013 | Weir | |
| 2013/0138023 A1 | 5/2013 | Lerro | |
| 2013/0261516 A1 | 10/2013 | Cilea | |
| 2013/0281897 A1* | 10/2013 | Hoffmann | A61B 8/0816 601/107 |
| 2014/0180331 A1 | 6/2014 | Turner | |
| 2014/0190023 A1* | 7/2014 | Vitantonio | B23D 49/006 30/369 |
| 2015/0005682 A1* | 1/2015 | Danby | A61H 23/0254 601/101 |
| 2015/0119771 A1 | 4/2015 | Roberts | |
| 2015/0148592 A1 | 5/2015 | Kanbar | |
| 2015/0375315 A1 | 12/2015 | Ukai | |
| 2016/0112841 A1 | 4/2016 | Holland | |
| 2017/0156974 A1 | 6/2017 | Griner | |
| 2018/0200141 A1 | 7/2018 | Wersland | |
| 2018/0236572 A1 | 8/2018 | Ukai | |
| 2018/0243158 A1 | 8/2018 | Loghmani | |
| 2018/0279843 A1 | 10/2018 | Paul | |
| 2018/0296433 A1 | 10/2018 | Danby | |

FOREIGN PATENT DOCUMENTS

| | | |
|---|---|---|
| JP | 1995051393 | 2/1995 |
| JP | 003077837 | 6/2001 |
| JP | 2005204777 | 4/2005 |
| JP | 2010534110 | 11/2010 |
| KR | 101123926 | 4/2012 |
| WO | 2009014727 | 1/2009 |
| WO | 2014118596 | 8/2014 |
| WO | 2015038005 | 3/2015 |

OTHER PUBLICATIONS

PCT/US2018/022426 International Search Report & Written Opinion dated May 31, 2018.
AU 2016284030 Examination Report dated May 7, 2018.
JP2018-517683 Office Action dated Oct. 25, 2018.
CA 2990178 Office Action dated Oct. 25, 2018.
WORX Trans4mer "Safety and Operating Manual Original Instructions" for 12V Li-Ion Multi-purpose saw, WX540, WX540.3, WX540.9, 2013.

(56) References Cited

OTHER PUBLICATIONS

Rachel [no family name indicated], "Jigsaw Massager", Apr. 18, 2010 (https://web.archive.org/web/20100418041422/http://www.instructables.com/id/Jigsaw-Massager/).
Rockwell Trans4mer Operating Manual for Multi-purpose saw, Model RK2516/RK2516K, 2011.
PCT/US2020/031936 International Search Report & Written Opinion dated Sep. 11, 2020.
PCT/US2020/50399 International Search Report & Written Opinion dated Feb. 4, 2021.

* cited by examiner

PERCUSSIVE THERAPY DEVICE WITH VARIABLE AMPLITUDE

CROSS-REFERENCE TO RELATED APPLICATIONS

This application is a continuation-in-part of U.S. patent application Ser. No. 16/869,402, filed May 7, 2020, which is a continuation-in-part of U.S. patent application Ser. No. 16/675,772, filed Nov. 6, 2019, now U.S. Pat. No. 10,702,448, which is a continuation-in-part of U.S. patent application Ser. No. 16/357,984, filed Mar. 19, 2019, which is a continuation of U.S. patent application Ser. No. 15/920,322, filed on Mar. 13, 2018, now U.S. Pat. No. 10,357,425, which is a continuation-in-part of U.S. patent application Ser. No. 15/458,920, filed on Mar. 14, 2017, which is a continuation-in-part of Ser. No. 15/186,859, filed on Jun. 20, 2016, which claims the benefit of U.S. Provisional Patent Application No. 62/182,525, filed on Jun. 20, 2015. U.S. patent application Ser. No. 16/675,772 also claims the benefit of U.S. Provisional Patent Application No. 62/785,151, filed on Dec. 26, 2018, U.S. Provisional Patent Application No. 62/844,424, filed on May 7, 2019, and U.S. Provisional Patent Application No. 62/899,098, filed on Sep. 11, 2019. This application also claims the benefit of U.S. Patent Application No. 63/044,860, filed Jun. 26, 2020 and U.S. Patent Application No. 63/065,114, filed Aug. 13, 2020. All applications listed above are incorporated by reference herein in their entireties.

FIELD OF THE INVENTION

The present invention relates generally to massage devices and more particularly to a percussive therapy device with variable amplitude.

BACKGROUND OF THE INVENTION

Percussive massage devices typically only include a single reciprocating amplitude or stroke. However, different amplitudes may provide different levels or types of massage. Accordingly, a need exists for a percussive massage device with the ability to vary the amplitude.

SUMMARY OF THE PREFERRED EMBODIMENTS

In accordance with a first aspect of the present invention there is provided a percussive therapy device that includes a housing, an electrical source, a motor positioned in the housing, a switch for activating the motor, a push rod assembly operatively connected to the motor and configured to provide reciprocating motion in response to activation of the motor, and a massage attachment secured to a distal end of the push rod assembly. The reciprocating motion of the push rod assembly has a user-adjustable amplitude. In a preferred embodiment, the distal end of the push rod assembly reciprocates within a first range and the amplitude is user-adjustable such that the distal end reciprocates within a second range. The second range is different than the first range. In a preferred embodiment, the device includes an input that changes the amplitude from the first range to the second range.

In a preferred embodiment, the percussive therapy device includes a variable amplitude assembly that includes an eccentric weight member. The eccentric weight member is operatively connected to the motor. In an embodiment, the motor includes a motor shaft operatively connected to the eccentric weight member. In another embodiment, the eccentric weight member may include a shaft that is received in the motor. The motor is configured to rotate the eccentric weight member about a first axis in a first direction and an opposite second direction. When the eccentric weight member is rotated in the first direction the distal end of the push rod assembly reciprocates within the first range, and when the eccentric weight member is rotated in the second direction the distal end of the push rod assembly reciprocates within the second range. Preferably, the variable amplitude assembly includes a movable member that is movable with respect to the eccentric weight member between a first position and a second position. The movable member includes an offset shaft extending therefrom to which the push rod assembly is operatively connected. The distal end of the push rod assembly reciprocates within the first range when the movable member is in the first position and the distal end of the push rod assembly reciprocates within the second range when the movable member is in the second position. The movable member is movable from the first position to the second position when the rotation of the eccentric weight and/or motor shaft is reversed from the first direction to the second direction and vice versa. Preferably, at least one slot is defined in the eccentric weight member. The movable member includes a main body portion with a slide member extending therefrom. The slide member is received in and movable within the slot. In another embodiment, the movable member can include the slot and the slide member can extend from the eccentric weight member.

In a preferred embodiment, the variable amplitude device includes an interference member that is positioned in a channel defined in the eccentric weight member. The interference member is movable between a deployed position and a rest position. In one of the deployed position or the rest position the interference member prevents the movable member from moving between the first position and the second position, and in the other of the deployed position and the rest position the interference member does not prevent the movable member from moving between the first position and the second position. In an embodiment where in the deployed position the interference member prevents the movable member from moving between the first position and the second position and in the rest position the interference member does not prevent the movable member from moving between the first position and the second position, the interference member is biased to the rest position by a spring. In this embodiment, the interference member is movable from the rest position to the deployed position when the eccentric weight member and/or motor shaft rotates at a predetermined RPM. This movement is due to the weight of the interference member and the centripetal force created as rotational speed increases. In a preferred embodiment, the interference member includes a stop member and the movable member includes a tooth. In the deployed position the stop member blocks the tooth to prevent the movable member from moving between the first position and the second position.

In a preferred embodiment, the interference member is movable from the rest position to the deployed position (or vice versa) by the activation of an electromagnet. In the embodiment with the electromagnet, the interference member may include a stop member and the movable member includes a tooth, and in the rest position the stop member blocks the tooth to prevent the movable member from moving between the first position and the second position.

In accordance with another aspect of the present invention there is provided a method of using a percussive therapy device that includes a housing, an electrical source, a motor positioned in the housing, a switch for activating the motor, a push rod assembly operatively connected to the motor and configured to provide reciprocating motion in response to activation of the motor, and a massage attachment secured to a distal end of the push rod assembly. The method includes (a) activating the motor and massaging a body part with the massage attachment, where the distal end of the push rod assembly reciprocates within a first range, (b) adjusting an amplitude of the reciprocation, and (c) activating the motor and massaging the body part with the massage attachment, where the distal end of the push rod assembly reciprocates within a second range. The second range is different than the first range. In a preferred embodiment, the method includes the step of activating an input to adjust the amplitude. In a preferred embodiment, the motor includes a motor shaft, wherein during step (a) the motor shaft is rotated in a first direction, and wherein during step (c) the motor shaft is rotated in a second direction. In a preferred embodiment, the device includes an eccentric weight member that is rotated by the motor, wherein during step (a) the eccentric weight member is rotated in a first direction, and wherein during step (c) the eccentric weight member is rotated in a second direction. Preferably, the input causes the change in direction of the motor, thereby causing the amplitude to be varied.

In accordance with another aspect of the present invention there is provided a variable amplitude assembly that includes an eccentric weight member that is rotatable about a first axis in a first direction and an opposite second direction, and a movable member that is movable with respect to the eccentric weight member between a first position and a second position. The movable member includes an offset shaft extending therefrom that defines a second axis. The movable member is movable from the first position to the second position when the rotation of the eccentric weight member is reversed from the first direction to the second direction (and vice versa). The second axis is positioned closer to the first axis when the movable member is in the first position than when the movable member is in the second position.

It will be appreciated that the amplitude variability mechanisms and assemblies discussed herein can be used in any percussive massage device or other power tool where rotating motion is converted to reciprocating motion and an eccentric weight is used. For example, see U.S. Patent Publication No. 2020/0261307 (the "'307 publication") and U.S. patent application Ser. No. 16/824,328 (the "'328 application"), filed Mar. 19, 2020, the entireties of which are incorporated by reference herein. The percussive and/or vibration massage devices taught in the '307 publication and the '328 application include drive trains with motors that include a rotating motor shaft that rotates an eccentric weight and converts the rotating motion of the motor shaft into reciprocating motion of a push rod assembly that is associated with the eccentric weight. The eccentric weight includes a shaft on which is attached a push rod, which is pivotally connected to an output or reciprocating shaft, which includes a massage attachment on the end thereof. The present invention can be utilized in these drive trains to vary the amplitude (ultimately of the massage attachment). The present invention can also be used in other power tools that include reciprocating motion, such as reciprocating saws and the like.

In a preferred embodiment, the percussive massage device includes the ability to vary the amplitude, thus providing a longer or shorter stroke depending on the application or needs of the user. For example, the device can include a mechanical switch that allows the eccentricity of the connector or moveable member with an offset shaft (or pin structure) to be modified (e.g., between 4 mm and 8 mm). The mechanism can include a push button and a slider. The moveable member (that includes the pin structure) has a spring that lets it fall back into the locked position. The amplitude variability can also be part of the routines or presets taught in the '307 publication. In other words, during the routine, the amplitude can automatically be varied.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

Figure 1:
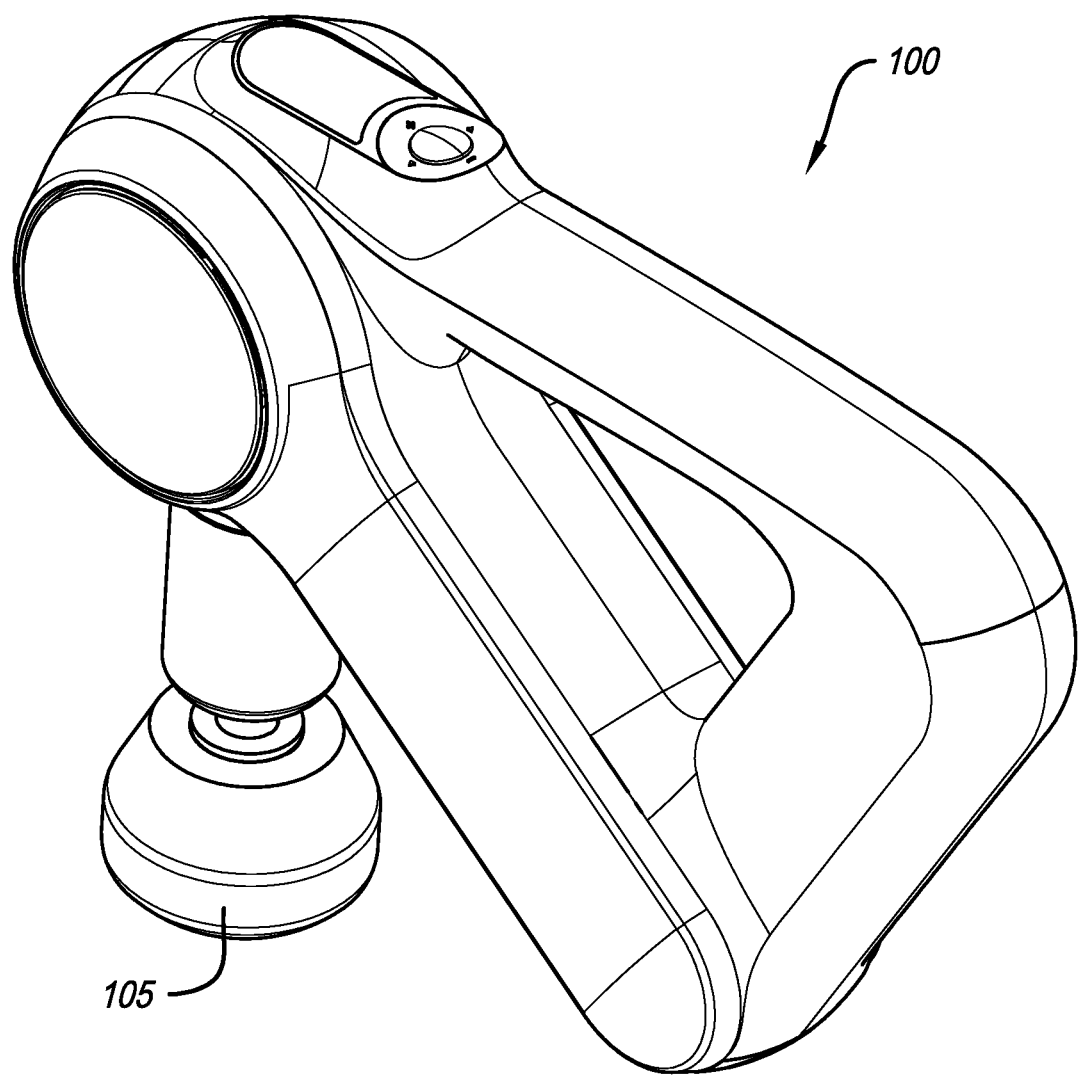
FIG. 1 is a perspective view of a first percussive massage or therapy device that includes a drive train that includes the ability to vary the amplitude in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or another embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. Appearances of the phrase "in one embodiment" in various places in the specification do not necessarily refer to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," and "below" used herein are merely for ease of description and refer to the orientation of the components as shown in the figures. It should be understood that any orientation of the components described herein is within the scope of the present invention.

Figure 2:
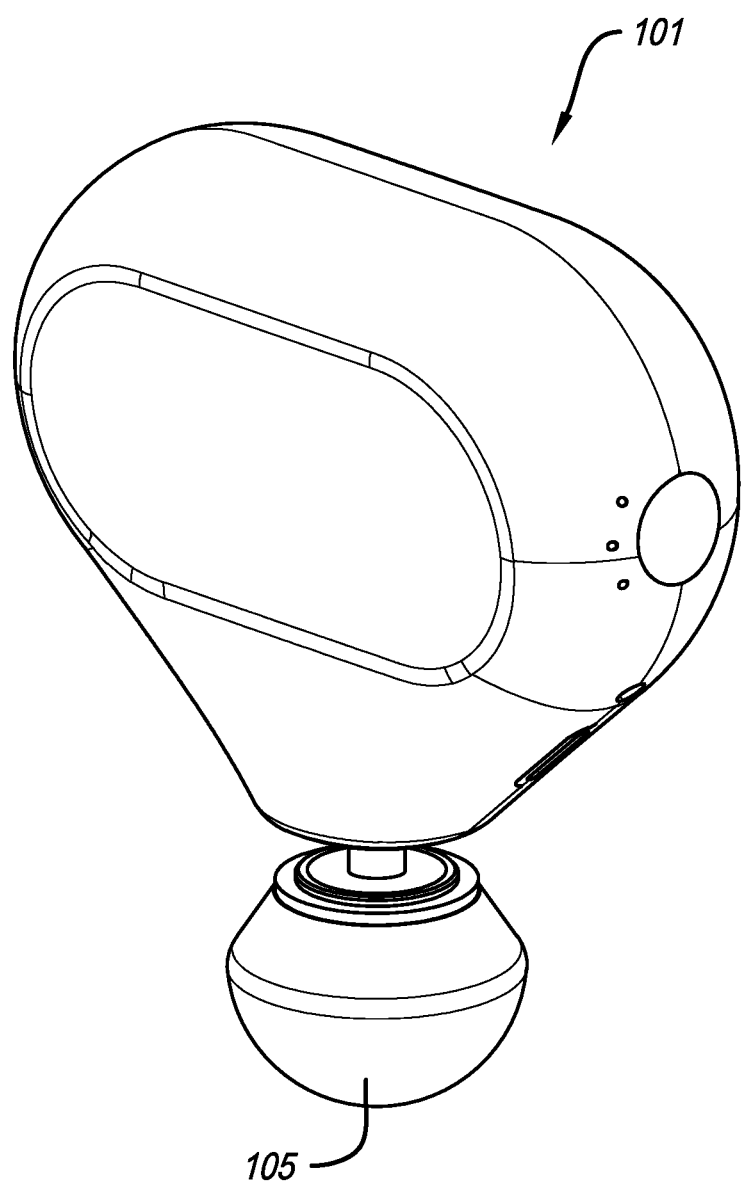
FIG. 2 is a perspective view of a second percussive massage or therapy device that includes a drive train that includes the ability to vary the amplitude.
Figure 3:
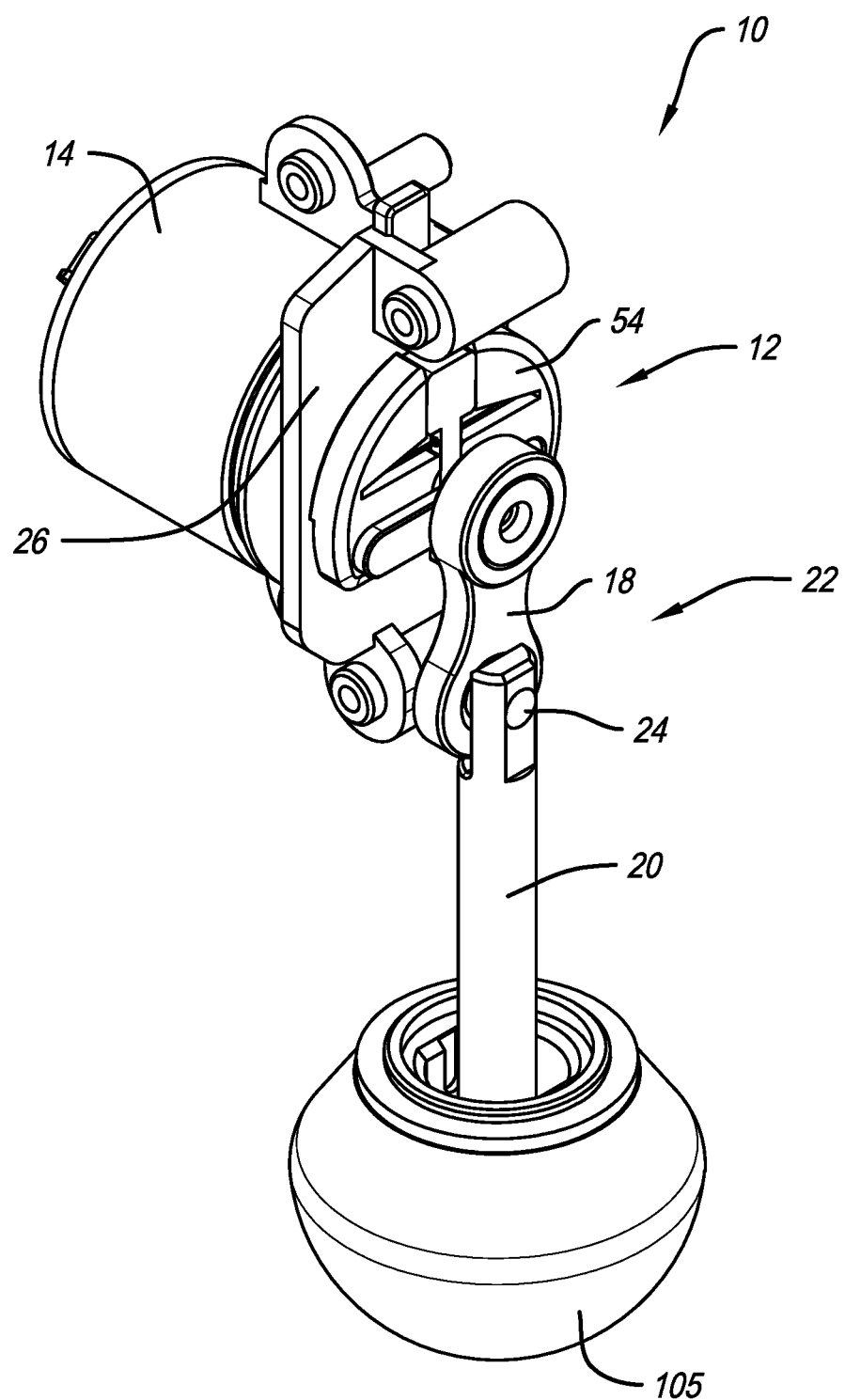
FIG. 3 is a perspective view of a drive train that includes the ability to vary the amplitude in accordance with a preferred embodiment of the present invention.
Figure 4:
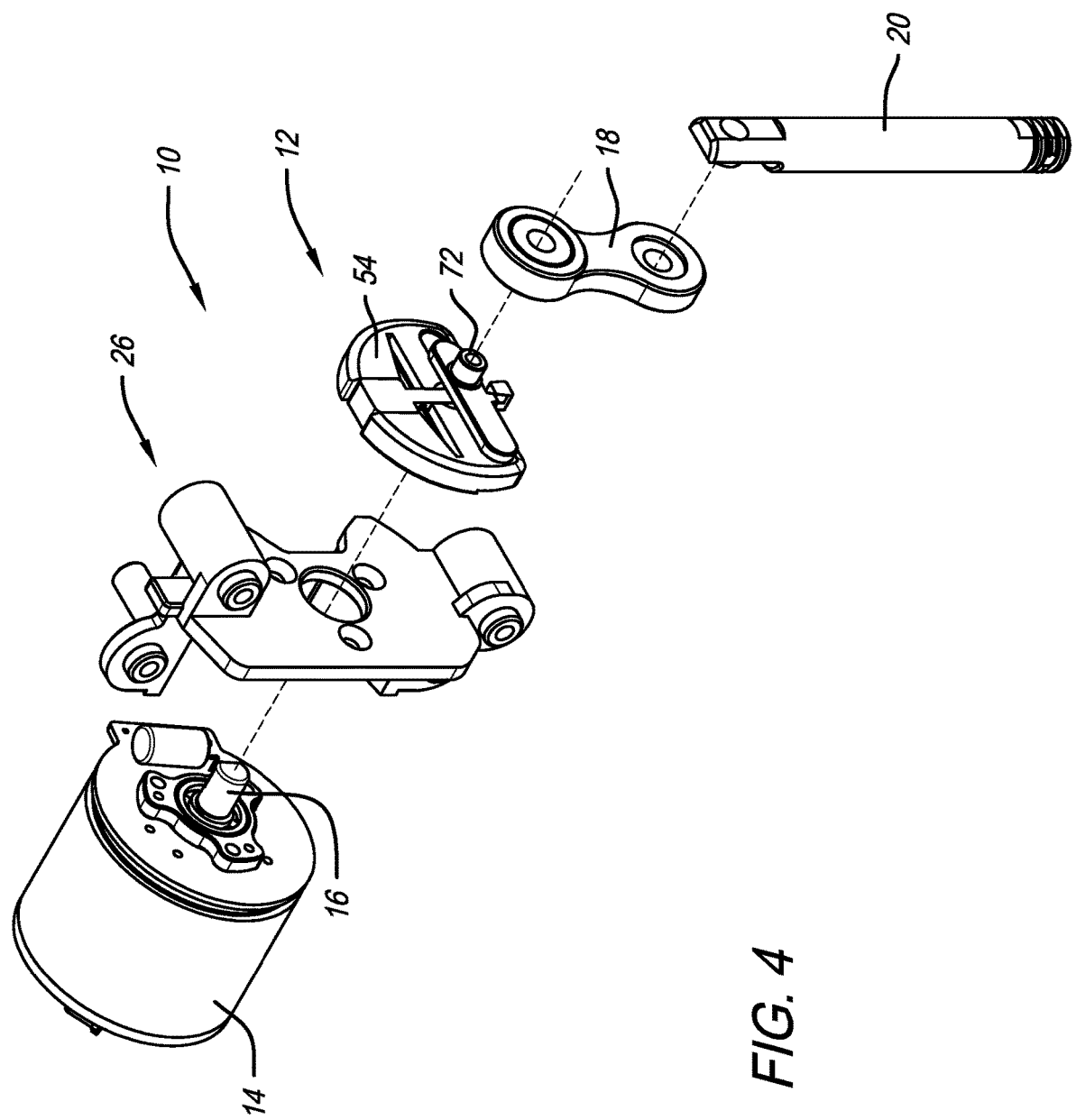
FIG. 4 is an exploded perspective view of the drive train.

Described herein is a system and assembly for varying the amplitude or stroke in percussive massage or therapy devices. Referring now to the drawings, which are for purposes of illustrating the present invention and not for purposes of limiting the same, the drawings show a drive train assembly 10 that includes a variable amplitude assembly 12 that can be used in various percussive massage devices. FIGS. 1 and 2 show different types of percussive massage devices 100 and 101 in which the variable amplitude assembly 12 can be used. The drive train assembly 10 shown in FIG. 3 and other figures is the particular one that can be used in percussive massage device 101.

As shown in FIGS. 3-13, the drive train assembly 10 generally includes the variable amplitude assembly 12, motor 14, motor shaft 16, push rod 18 and reciprocating shaft 20. The rotation of the motor shaft 16 is converted to reciprocating motion of the reciprocating shaft 20 via a linkage assembly (or push rod assembly) 22 that includes the push rod 18 that is pivotably connected to the reciprocating shaft 20 (see pivot pin 24) and a counterweight or an eccentric weight member 54 that is part of the variable amplitude assembly 12. An offset shaft 72 is operatively connected (e.g., pivotably connected) to the push rod 18. It will be appreciated that the axis of the offset shaft 72 is offset from the axis of rotation of the motor shaft 32. In a preferred embodiment, the motor 14 is mounted on a motor mount 26.

Figure 5:
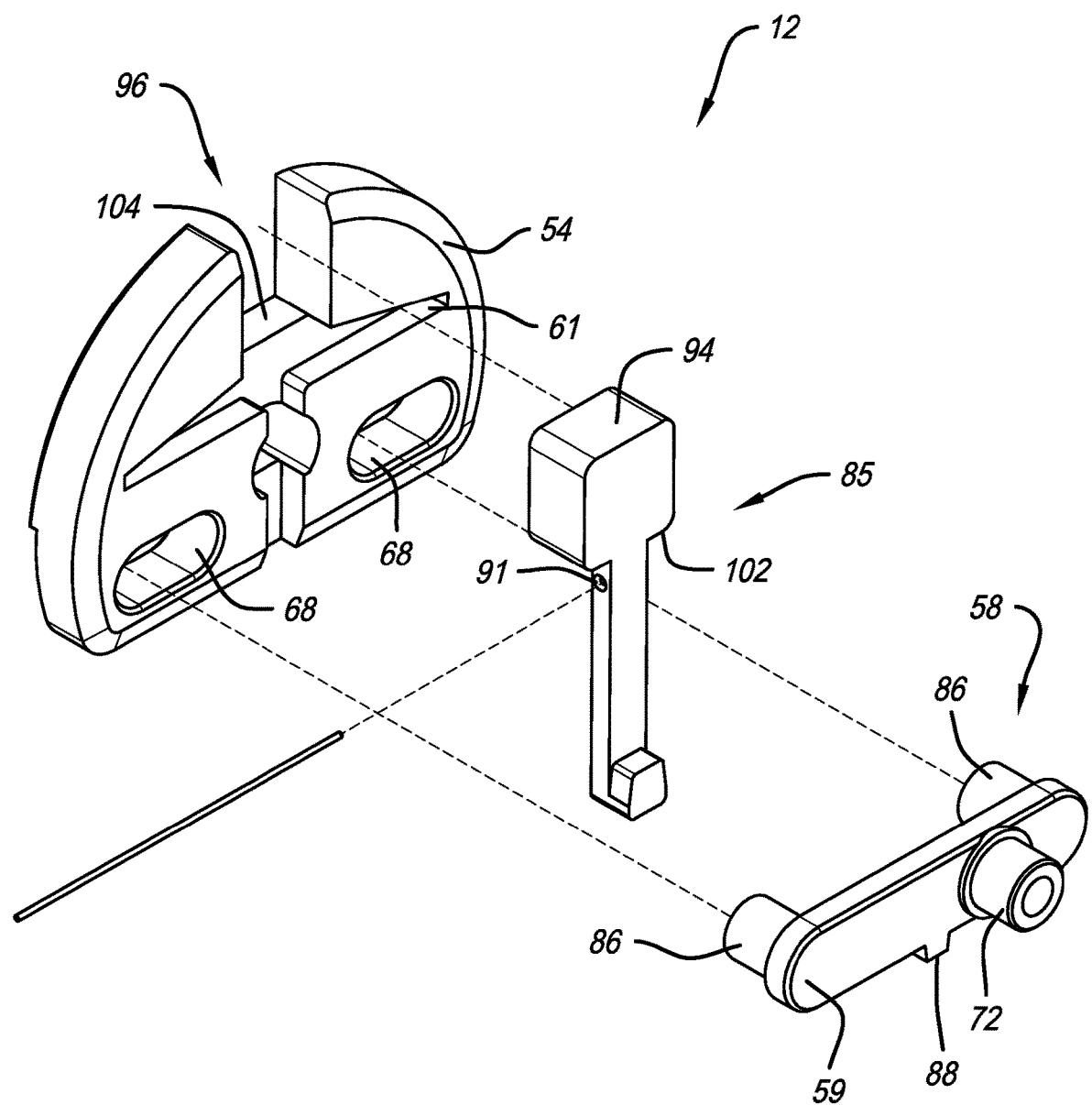
FIG. 5 is an exploded perspective view of a variable amplitude assembly in accordance with a preferred embodiment of the present invention.
Figure 6:
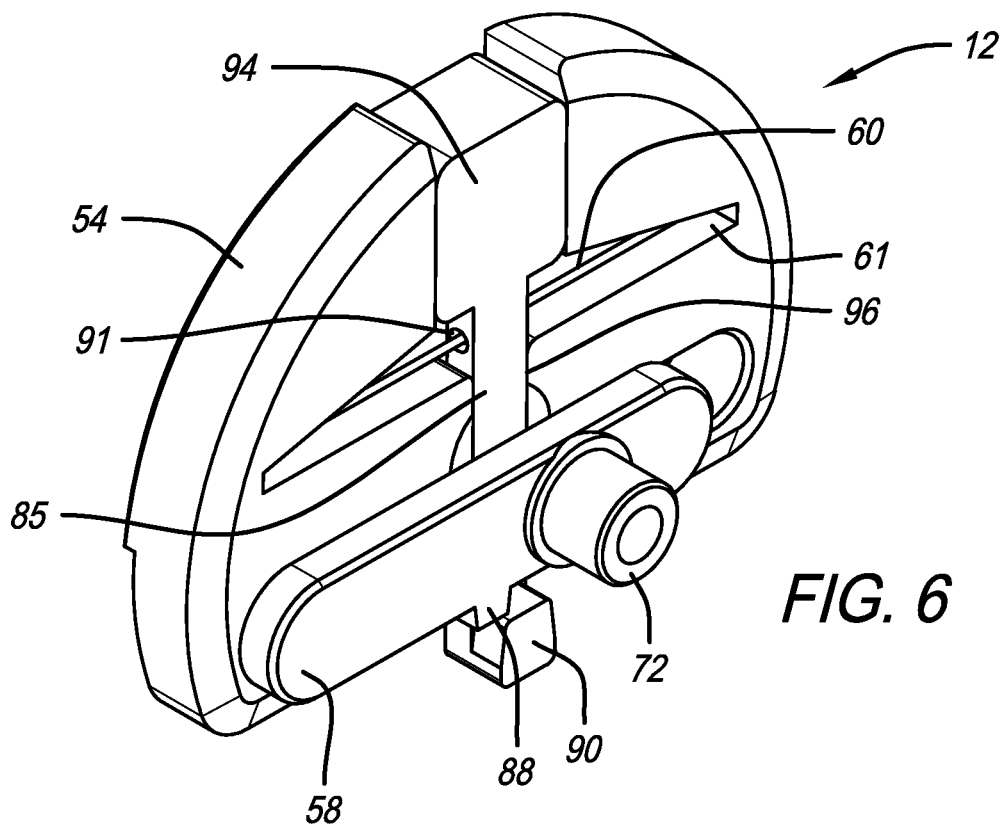
FIG. 6 is a perspective view of the variable amplitude assembly.
Figure 7:
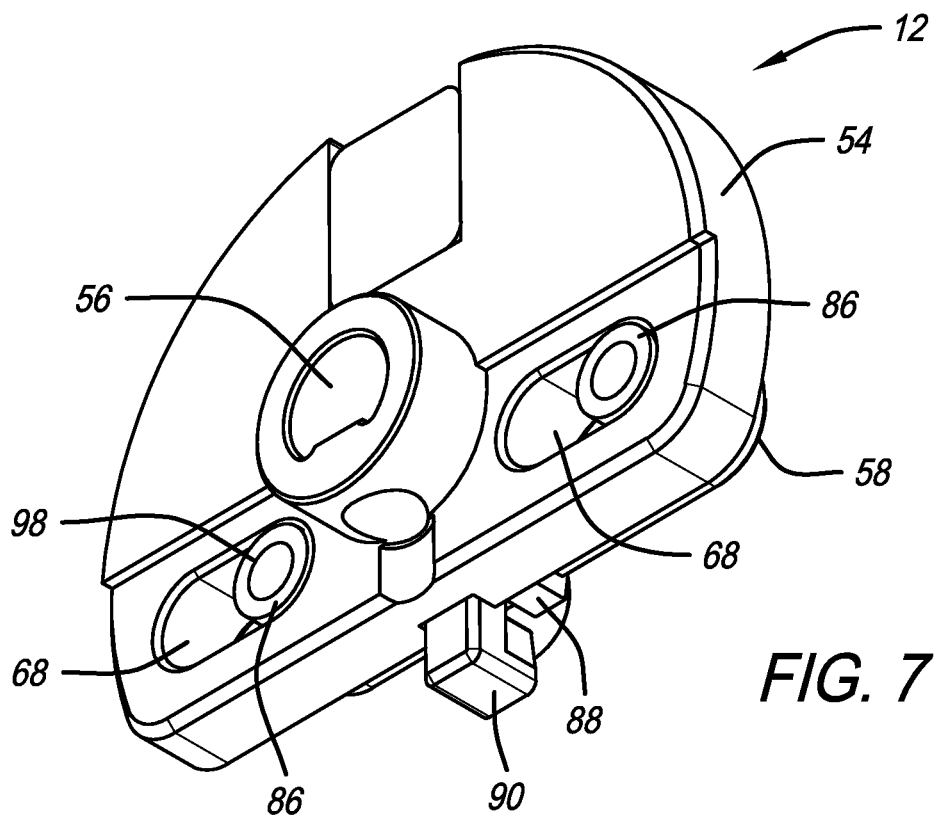
FIG. 7 is a perspective view of the variable amplitude assembly shown from the other side as FIG. 6.

As shown in FIG. 5-7, The variable amplitude assembly 12 includes the eccentric weight member 54 and a shaft opening 56 therein that receives the rotating drive shaft of the motor, an interference member 85, a movable member 58 and a spring 60 (preferably a spring) that is received in a spring channel 61. As shown in FIG. 5, the movable member 58 includes a main body portion 59, two slide members 86 that are received in slots 68 that are defined in the eccentric weight member 54, the offset shaft 72 and a tooth 88 that interacts with a stop member 90 on the interference member 85. The interference member also includes an opening 91 defined therein through which the spring 60 extends, and a weight 94 further described below. The interference member 85 is received in and seated in a channel 96 defined in the eccentric weight member 54. Fasteners (e.g., threaded fasteners) can be received in threaded openings 98 in the slide members 86 to secure the movable member 58 to the eccentric weight member 54. The ends of the spring 60 are received in openings defined in the eccentric weight member that are positioned near the ends of the spring channel 61.

Figure 8:
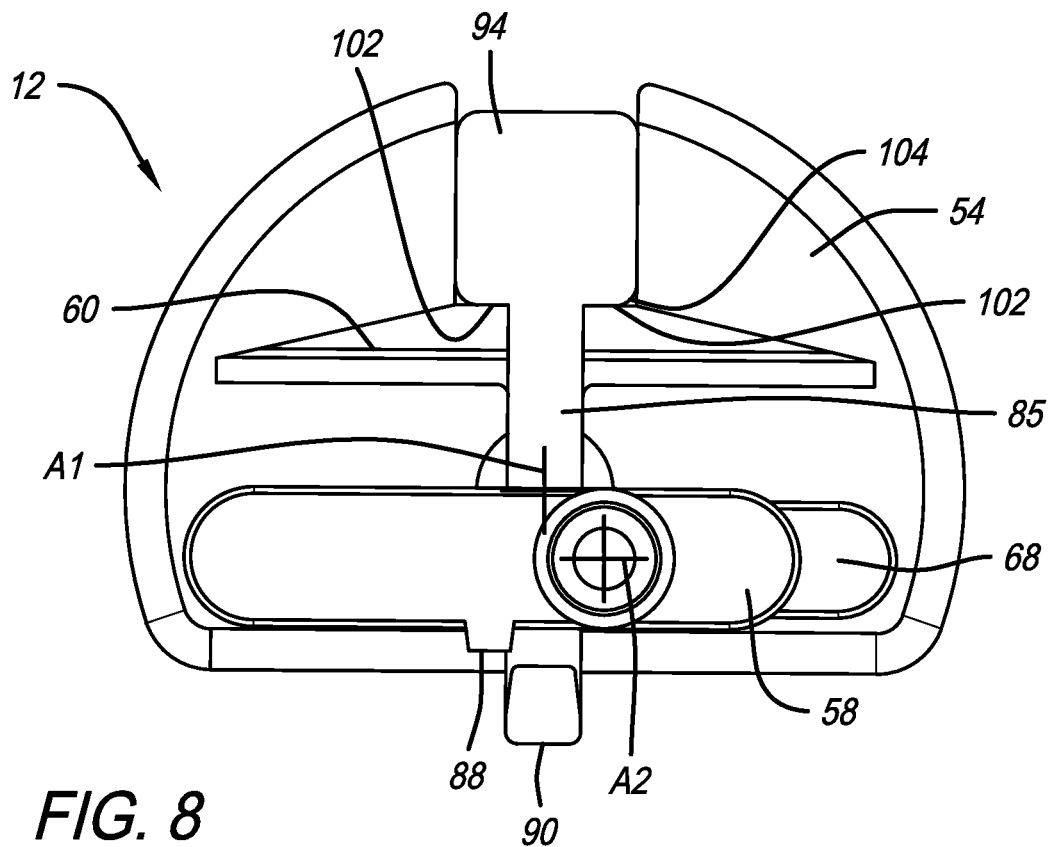
FIG. 8 is an elevational view of the variable amplitude assembly showing the movable member in the first position and the interference member in the rest position.
Figure 9:
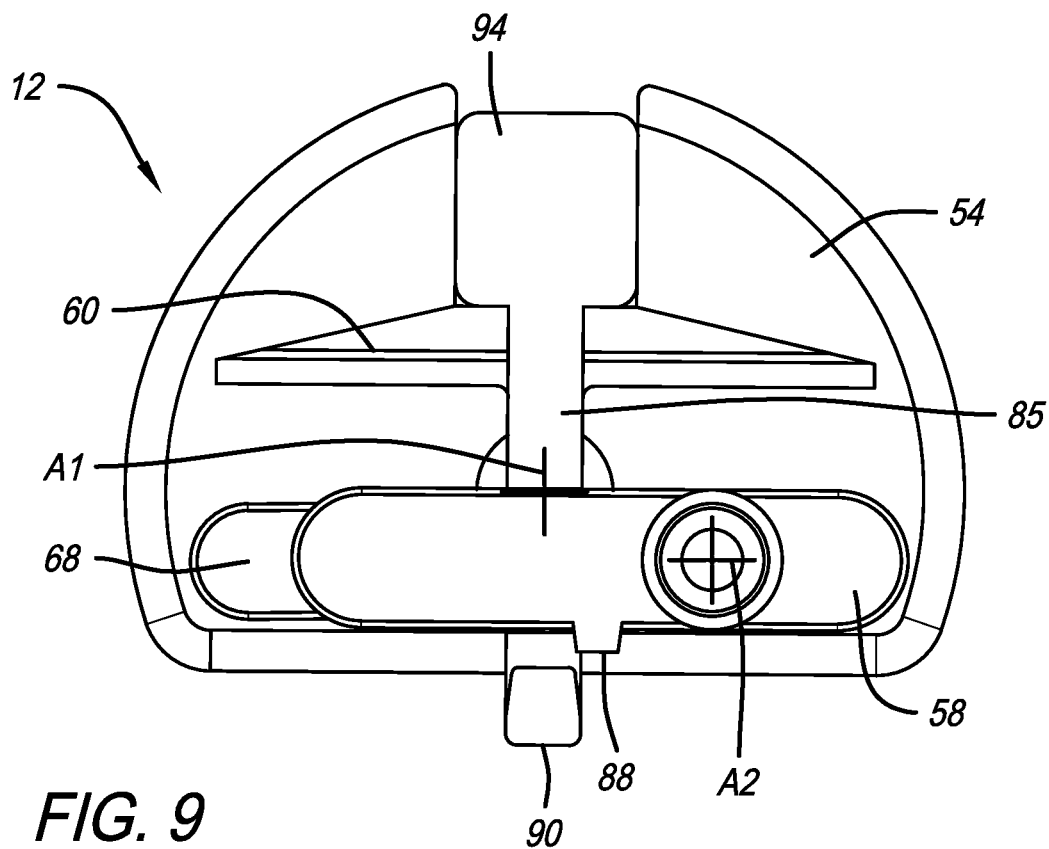
FIG. 9 is an elevational view of the variable amplitude assembly showing the movable member in the second position and the interference member in the rest position.
Figure 10:
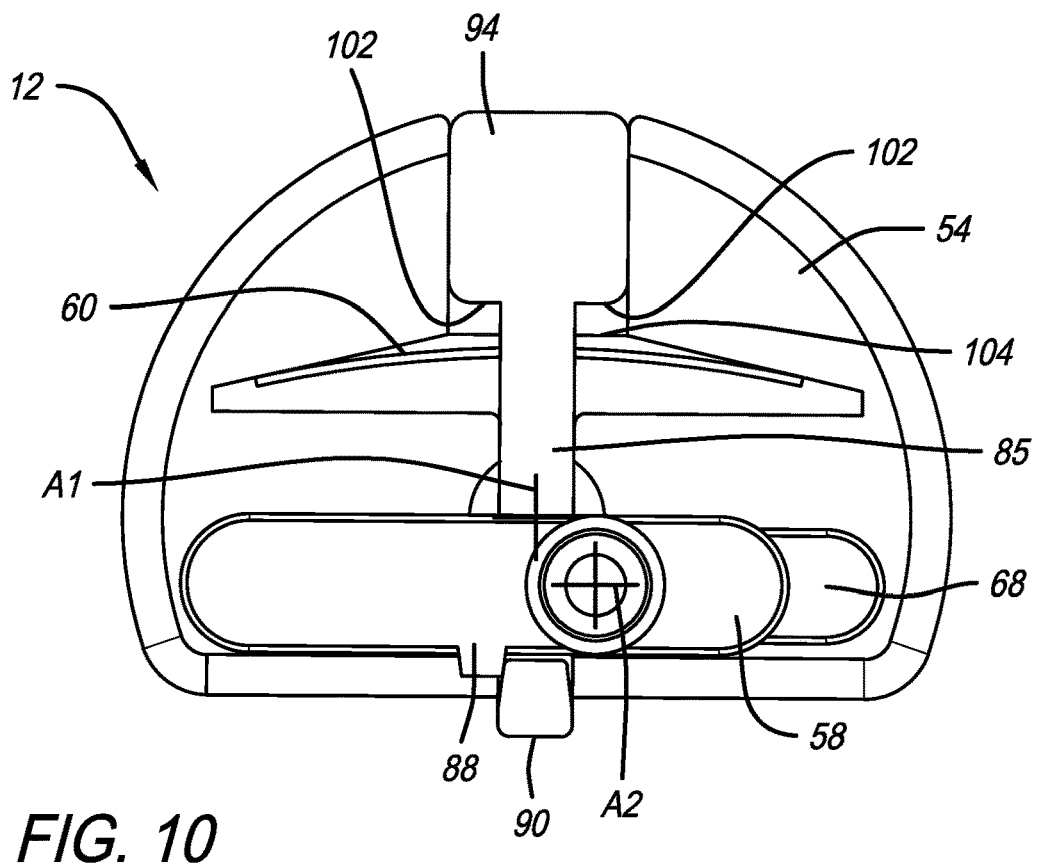
FIG. 10 is an elevational view of the variable amplitude assembly showing the movable member in the first position and the interference member in the deployed position.
Figure 11:
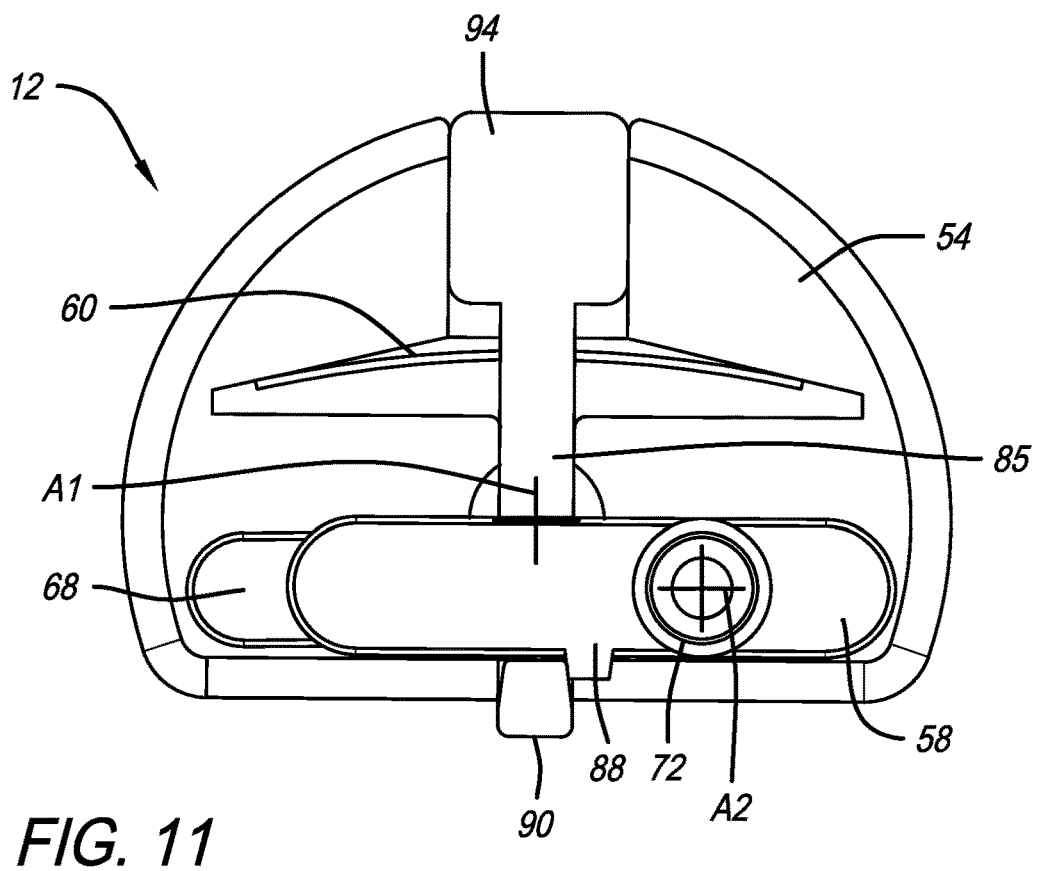
FIG. 11 is an elevational view of the variable amplitude assembly showing the movable member in the second position and the interference member in the deployed position.

FIGS. 8-11 show the different positions of the movable member 58 and the interference member 85. The movable member 58 is movable or slidable between a first position (FIGS. 8 and 10) and a second position (FIGS. 9 and 11). The interference member 85 is movable or slidable between a rest position (FIGS. 8 and 10) and a deployed position (FIGS. 9 and 11). Spring 60 biases the interference member 85 to the rest position. Shoulders 102 on the weight 94 contact stop surface 104 in the rest position (see FIG. 8).

Generally, the movable member 58 is located at the first position when the drive shaft of the motor is rotated in a first direction (clockwise or counterclockwise) and the movable member slides or translates to the second position when the drive shaft is reversed and begins to rotate in the opposite direction. When the motor is at rest and at the beginning of the rotation of the eccentric weight member in either direction, the interference member 85 remains in the rest position. In the rest position, the tooth 88 on the movable member 58 is not in engagement with and is spaced from stop member 90 such that movable member 58 can move linearly along slots 68 (FIGS. 8 and 10). During use, as the eccentric weight member 54 begins to rotate in the opposite direction from the previous use, the eccentric or centripetal force causes the movable member 58 to move to the other of the first or second position. As the eccentric weight member continues to rotate and speed up and reaches a desired RPM, the eccentric or centripetal force on the weight causes the interference member 85 to overcome the spring force of the spring 60 and the interference member 85 moves outwardly within channel 96, thereby causing the stop member 90 to move into the linear path of tooth 88, thus blocking linear movement of the tooth 88 and the movable member 58 and locking or securing the movable member FIGS. 9 and 11) in either the first or second position (depending on the rotational direction of the eccentric weight member 54).

Eccentric force causes the movable member 58 and the slide members 86 to move to the opposite end of the slots 68 when the motor is reversed. It will be appreciated that the movable member 58 will be located at the first position, as shown in FIGS. 8 and 10, when the eccentric weight member 54 is rotated counterclockwise (based on the configuration shown in FIGS. 8-11) and the movable member 58 will be located at the second position, as shown in FIGS. 9 and 11, when the eccentric weight member 54 is rotated clockwise (based on the configuration shown in FIGS. 8-11). Essentially, the opposite ends of slots 68 are stop members that stop the movable member 58 as it moves when the motor direction is reversed. In short, the direction of rotation of the motor drive shaft determines the amplitude of the reciprocating movement of the reciprocating shaft and, therefore, the massage attachment.

FIGS. 8 and 9 also show the axis of rotation A1 of the eccentric weight member 54 and the axis of offset shaft 72 A2. As can be seen in a comparison of FIG. 8 to FIG. 9, the distance between A1 and A2 is greater when the movable member 58 is in the second position than when the movable member 58 is in the first position. As a result, the reciprocating shaft 20 (and massage attachment 105) has a greater amplitude or stroke when the movable member 58 is in the second position than when the movable member 58 is in the first position. In an exemplary embodiment, the amplitude is 8 mm when the movable member is in the first position (A1 is 4 mm from A2) and 16 mm when the movable member is in the second position (A1 is 8 mm from A2). These numbers are only exemplary and the range can be wider or small than discussed above. In a preferred embodiment, shaft 72 (and A2) are positioned closer to one end of movable member 58 than the other to provide the different distances between A1 and A2 when the movable member is in the first and second positions. It will be appreciated that the drive train 50 can be used with any type of motor. The use of a brushless DC motor is not limiting on the invention.

Figure 12:
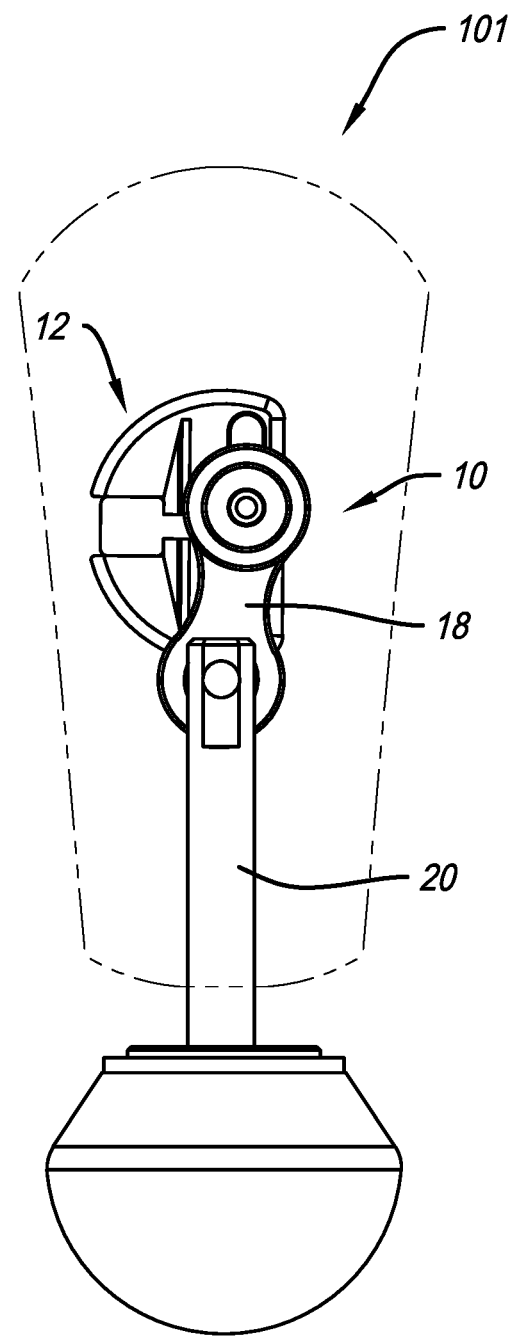
FIG. 12 is a side elevational view of the drive train in the second percussive therapy device and with the moveable member in the first position, thus providing a smaller amplitude.
Figure 13:
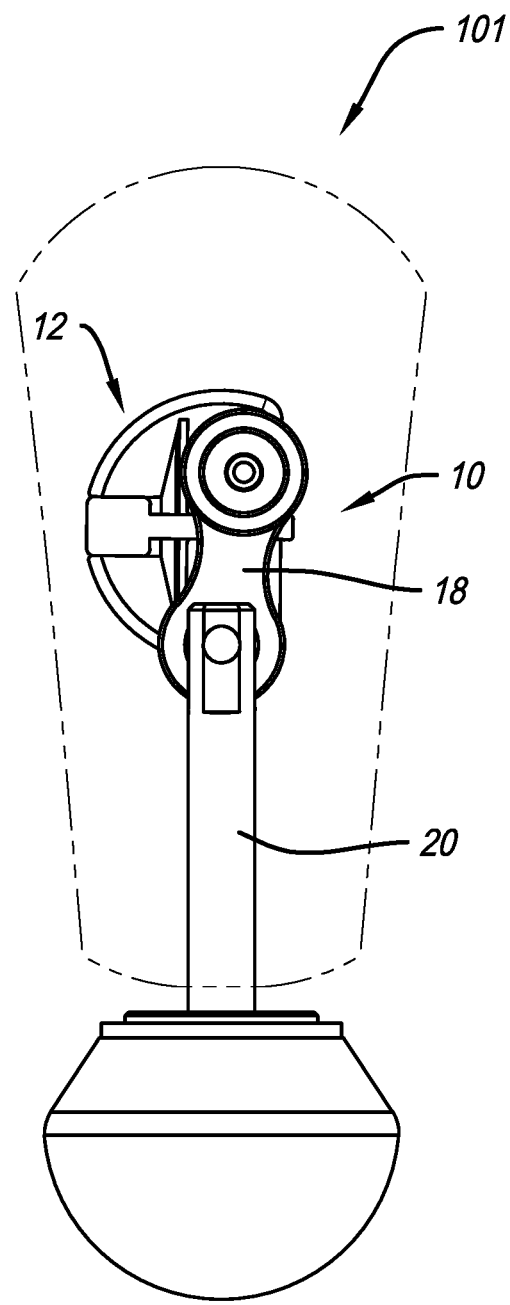
FIG. 13 is a side elevational view of the drive train in the second percussive therapy device and with the moveable member in the second position, thus providing a larger amplitude.

FIGS. 12 and 13 show the variable amplitude mechanism or assembly 12 in the drive train 10 of percussive massage device 101. FIG. 12 shows the variable amplitude assembly 12 with the movable member in the first position and FIG. 13 shows the variable amplitude assembly 12 with the movable member in the second position.

Figure 14:
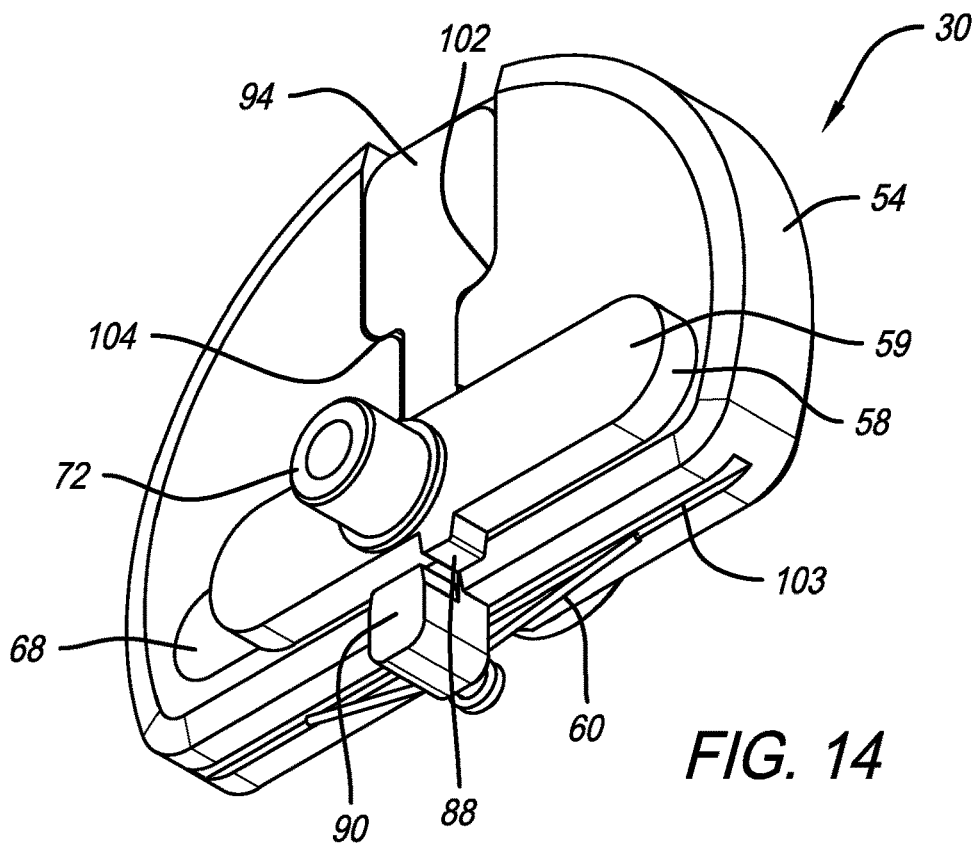
FIG. 14 is a perspective view of a variable amplitude assembly in accordance with a preferred embodiment of the present invention.

FIG. 14 shows another preferred embodiment of a variable amplitude assembly 30 that is a variation of the variable amplitude assembly 12 shown in FIGS. 3-13. Therefore, all text above related to the previous embodiment applies to this embodiment as well and all parts are interchangeable.

As shown in FIG. 14, variable amplitude assembly 30 includes the eccentric weight member 54, interference member 85, movable member 58 and spring 60 (preferably a torsion spring) that is received on a pin 92 that is part of and/or extends from the interference member 85. The movable member 58 includes shaft 72 that receives and, in use, reciprocates push rod 62 and tooth 88 that interacts with stop member 90 on the interference member 85. The interference member also includes a pin 92 that receives the coil portion of the spring 60 and a weight 94 further described below. The interference member 85 is received in and seated in channel 96 defined in the eccentric weight member 54. As shown in FIG. 14, the ends of the torsion spring 60 are received in and movable along a linear groove 103 defined in a side surface of the eccentric weight member 54. The positioning of the spring 60 is the biggest difference with the embodiment above. However, the spring 60 operates in the same manner as the spring in the embodiment shown FIGS. 3-13. Spring 60 biases the interference member 85 to the rest position. Shaft opening 56, and slide members 86 are not shown in FIG. 14, but are the same as shown in FIG. 7. The positioning of the movable member 58, offset shaft 72, interference member 85, axes A1 and A2 and related components shown in FIGS. 8-11 apply to variable amplitude assembly 30.

During use of variable amplitude assembly 30, as the eccentric weight member 54 begins to rotate in the opposite direction from the previous use, the eccentric or centripetal force causes the movable member 58 to move to the other of the first or second position. As the eccentric weight member continues to rotate and speed up and reaches a desired RPM, the eccentric or centripetal force on the weight causes the interference member 85 to overcome the spring force of the spring 60 and the interference member 85 moves outwardly within channel 96, thereby causing the stop member 90 to move into the linear path of tooth 88, thus blocking linear movement of the tooth 88 and the movable member 58 and locking or securing the movable member FIGS. 9 and 11) in either the first or second position (depending on the rotational direction of the eccentric weight member 54).

FIGS. 15-20 show another embodiment of a variable amplitude assembly 110 for use with a drive train in a percussive massage device for varying the amplitude of the output shaft and the massage element or attachment. Variable amplitude assembly 110 operates similarly to variable amplitude assemblies 12 and 30 above, but uses an electromagnet instead of the eccentric force to move the interference member 85. Therefore, all text herein related to the other embodiments discussed applies to this embodiment as well and all parts are interchangeable.

Figure 15:
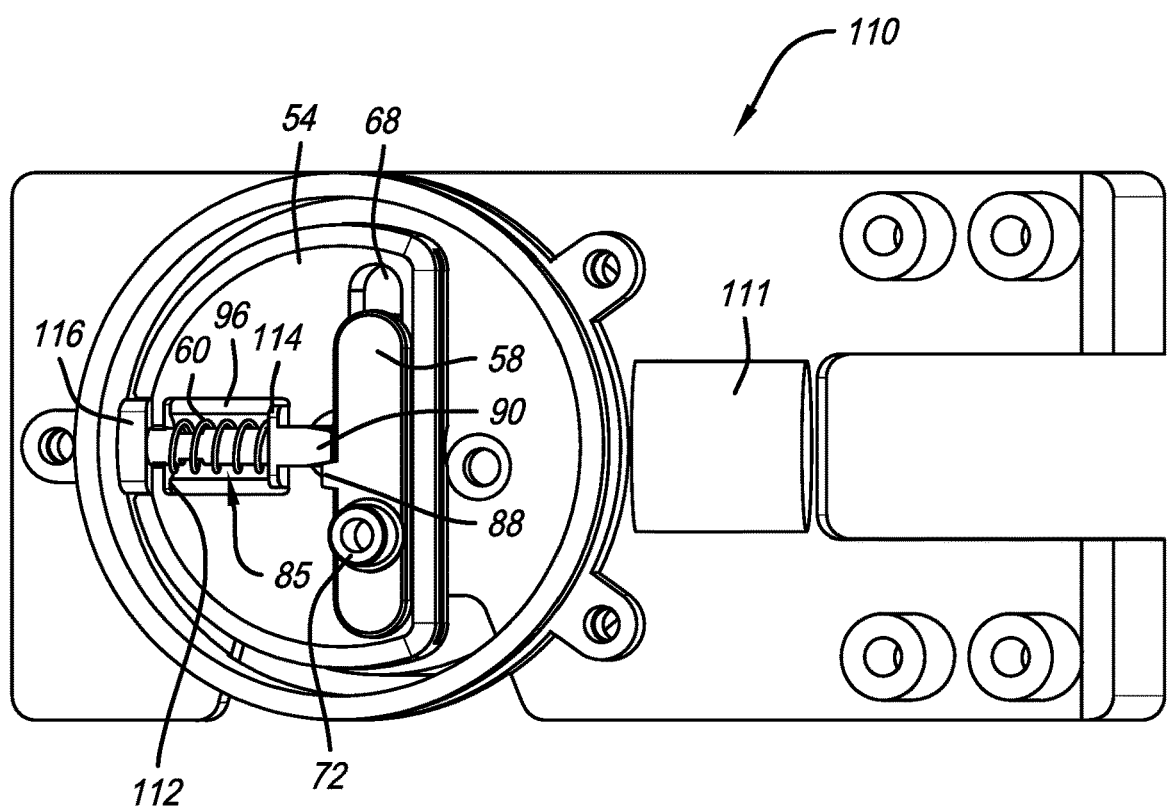
FIG. 15 is a perspective view of a variable amplitude assembly that includes an electromagnet in accordance with a preferred embodiment of the present invention.
Figure 16:
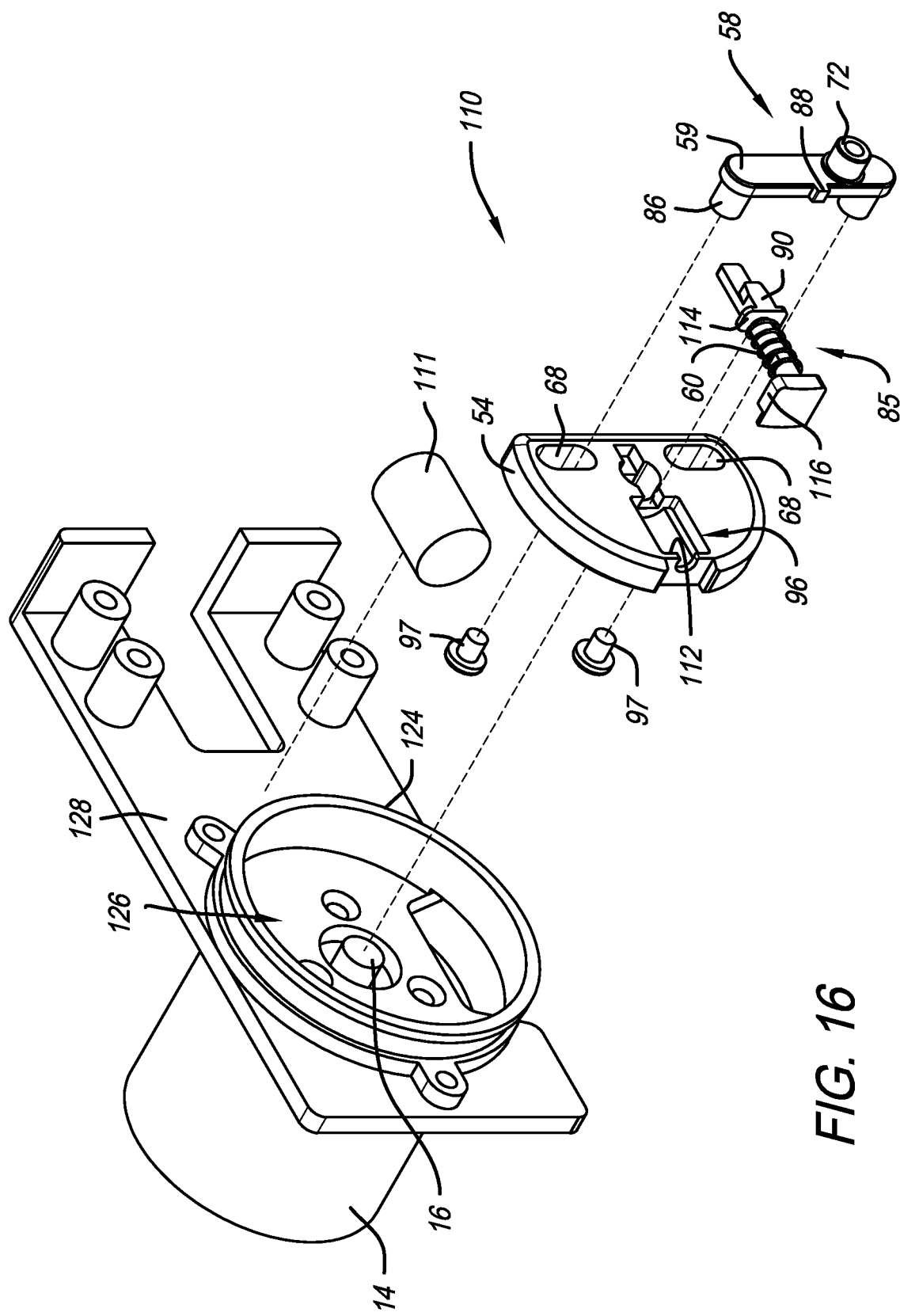
FIG. 16 is an exploded perspective view of the variable amplitude assembly of FIG. 15.

As shown in FIGS. 15-16, The variable amplitude assembly 110 includes eccentric weight member 54 and a shaft opening (not shown) therein that receives the rotating drive shaft 16 of the motor 14, an interference member 85, a movable member 58, and a spring 60 (preferably a coil spring). As shown in FIG. 16, the movable member 58 includes one or more slide members 86 that are received in slots 68 that are defined in the eccentric weight member 54, an offset shaft 72 that receives and, in use, reciprocates the push rod and a tooth 88 that interacts with a stop member 90 on the interference member 85. The interference member 85 is received in and extends through a channel 96 defined in the eccentric weight member 54. The spring 60 is received on a shaft portion of interference member 85 and extends between a first end 112 of channel 96 and an extension member 114 on the interference member 85. The interference member 85 includes a head portion 116. Threaded fastener(s) 97 are receive in threaded openings in the slide member(s) 86 and secure the movable member 58 to the eccentric weight member 54.

As shown in FIGS. 15 and 16, the variable amplitude assembly 110 includes an electromagnet 111. The electromagnet 111 is positioned outside a cylinder 124 on a mounting bracket 128. The cylinder 124 defines a rotation space 126 for the eccentric weight member 54. The electromagnet 111 is also positioned adjacent or close enough to head portion 116 of the interference member 85 that the electromagnet can pull the interference member radially outwardly and toward the electromagnet 111 when it is energized or turned on. Space is defined between the outer surface of the eccentric weight member 54 and the inner surface of the cylinder 124. This allows space for the head portion 116 (which is made of metal) to move outwardly and out of the head space defined in the eccentric weight member 54 in which it is seated. When the head portion 116 and the remainder of the interference member 85 is moved outwardly, the movable member 58 can move linearly, as described below.

Figure 17:
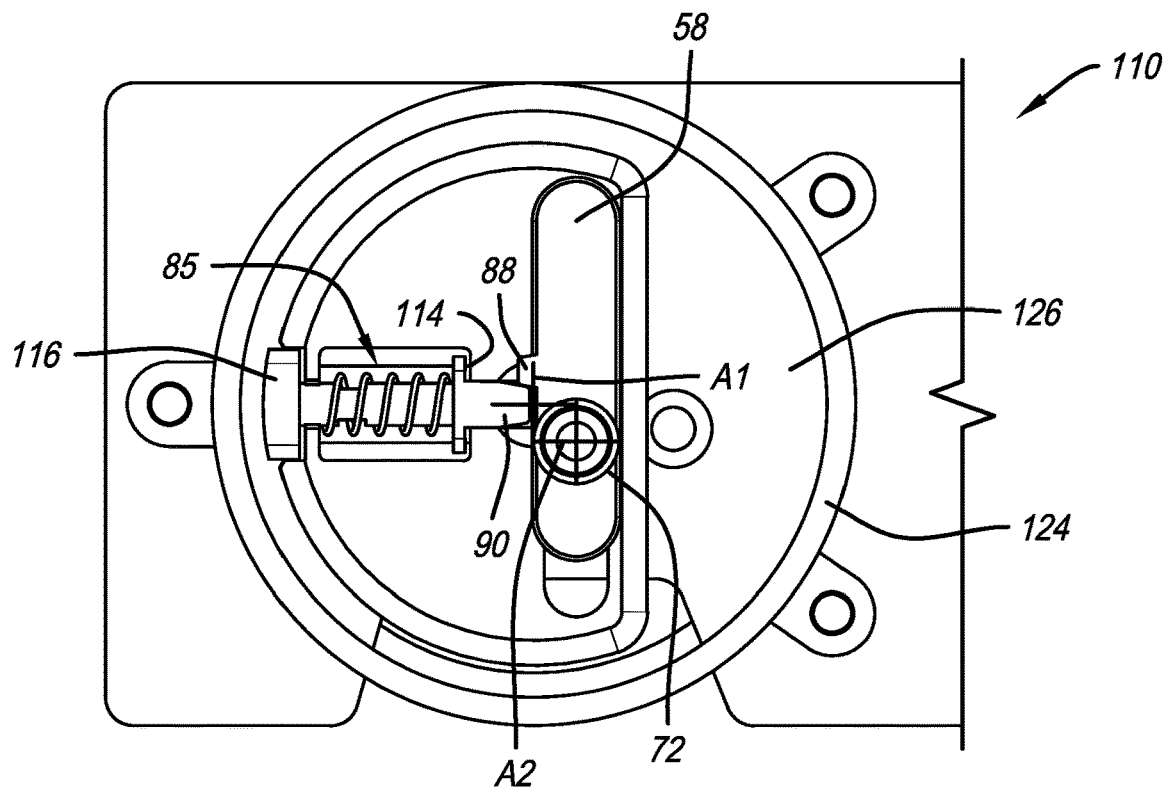
FIG. 17 is an elevational view of the variable amplitude assembly showing the movable member in the first position and the interference member in the rest position.
Figure 18:
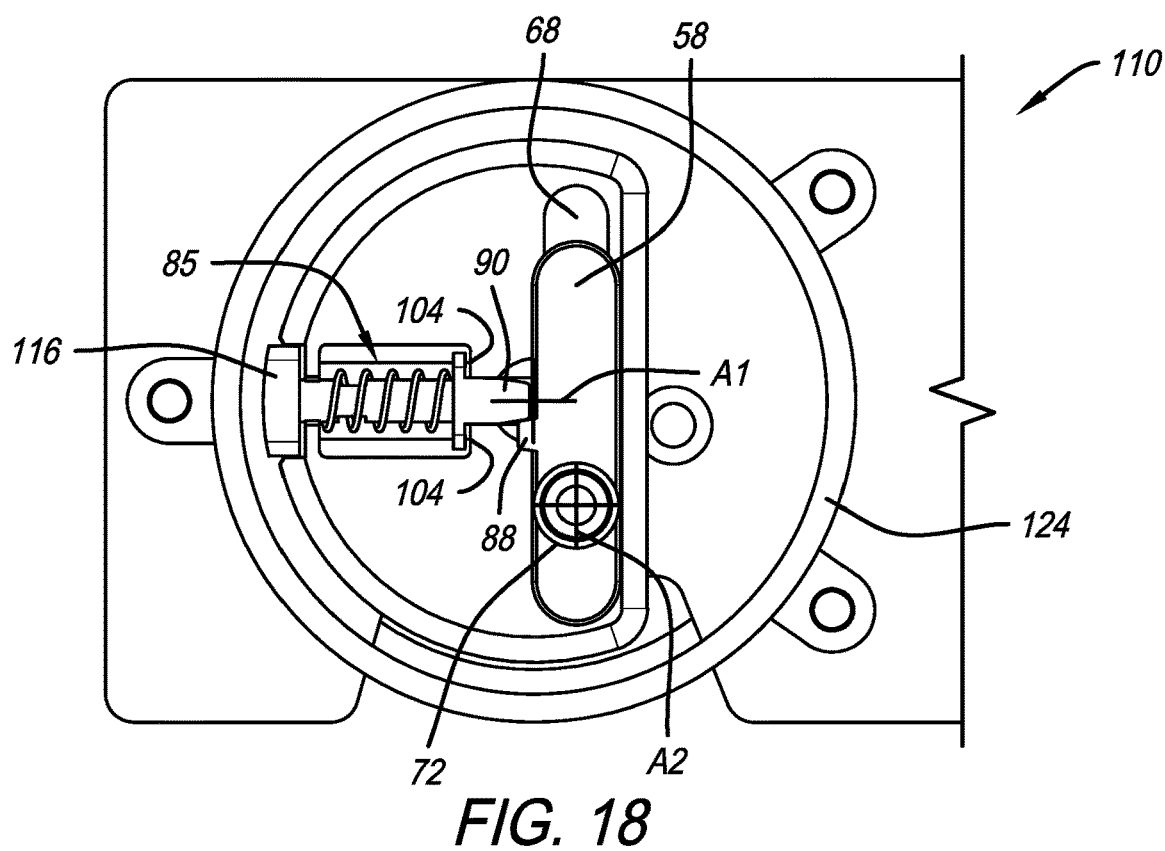
FIG. 18 is an elevational view of the variable amplitude assembly showing the movable member in the second position and the interference member in the rest position.
Figure 19:
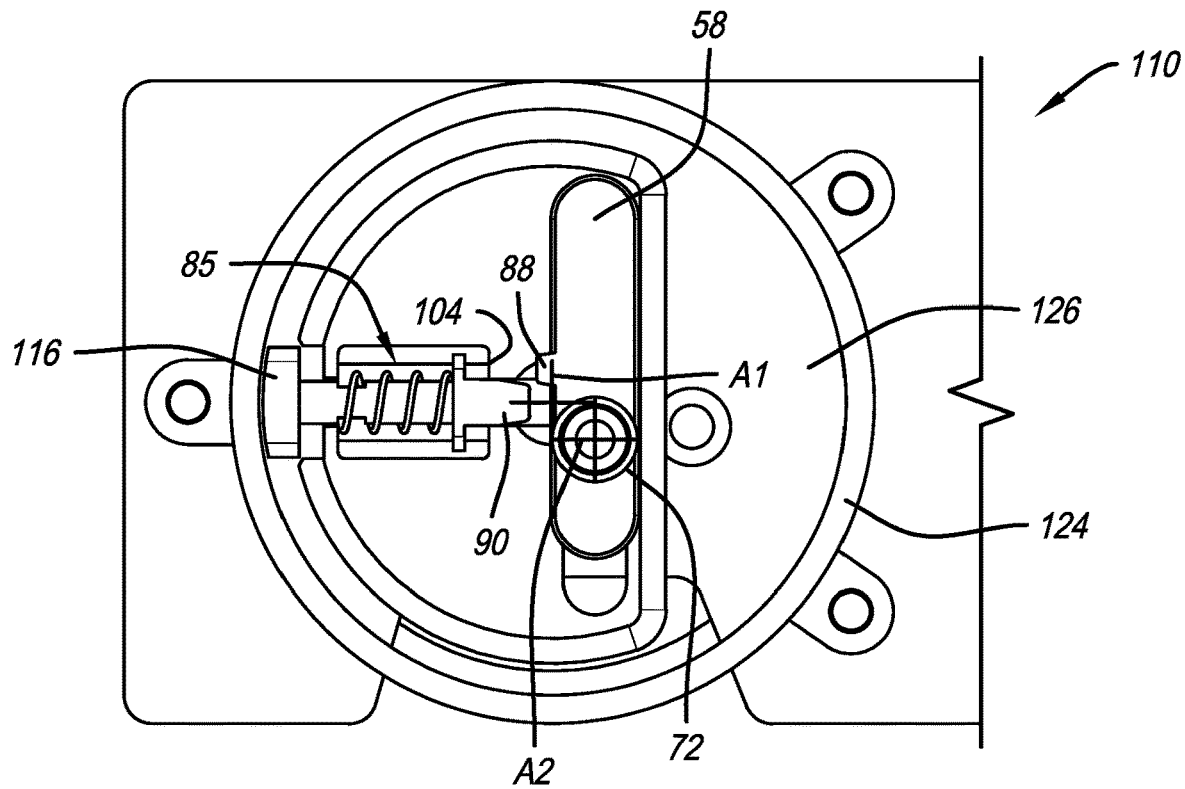
FIG. 19 is an elevational view of the variable amplitude assembly showing the movable member in the first position and the interference member in the deployed position.
Figure 20:
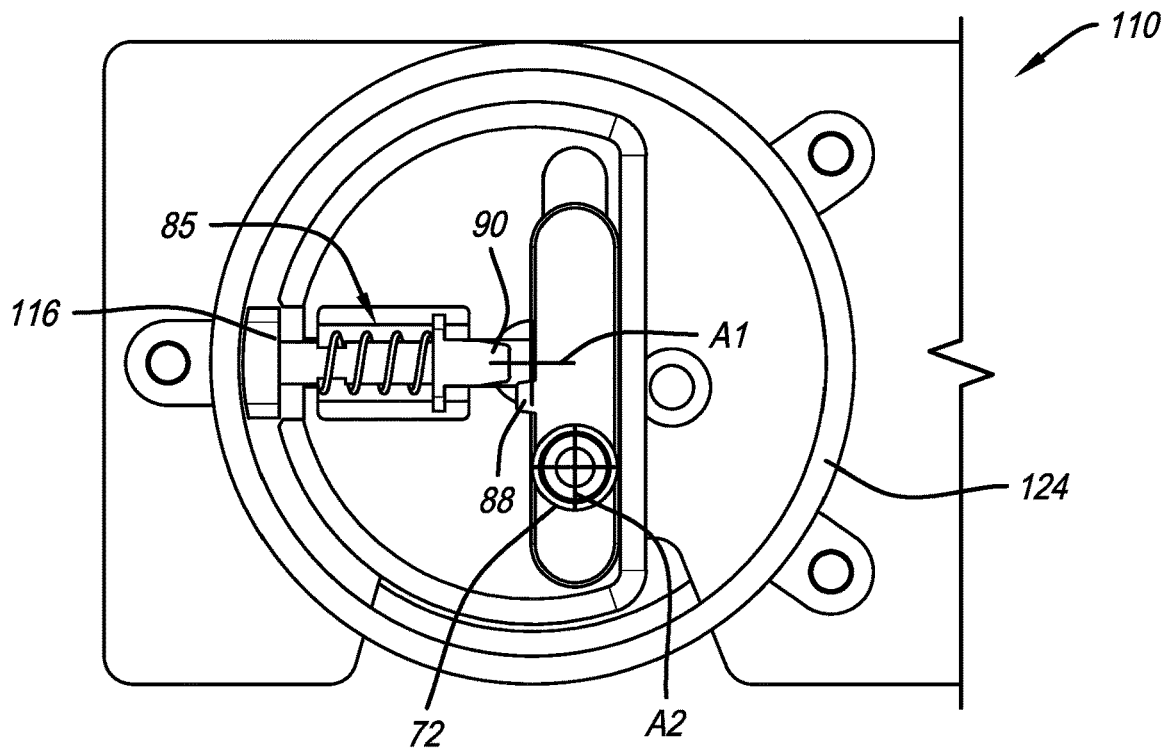
FIG. 20 is a side elevational view of the variable amplitude assembly showing the movable member in the second position and the interference member in the deployed position.

FIGS. 17-20 show the different positions of the movable member 58 and the interference member 85. The movable member 58 is movable or slidable between a first position (FIGS. 17 and 19) and a second position (FIGS. 18 and 20). The interference member 85 is movable or slidable between a rest position (FIGS. 17 and 18) and a deployed position (FIGS. 19 and 20). Spring 60 biases the interference member 85 to the rest position. The extension member(s) 114 contact stop surfaces 104 in the rest position (see FIG. 18).

Generally, the movable member 58 is located at the first position when the drive shaft of the motor is rotated in a first direction (clockwise or counterclockwise) and the movable member slides or translates to the second position when the drive shaft is reversed and begins to rotate in the opposite direction. When the motor 122 is at rest and at the beginning of the rotation of the eccentric weight member in either direction, the interference member 85 remains in the rest position. In the rest position, the tooth 88 on the movable member 58 engages with stop member 90 such that movable member 58 cannot move linearly along slots 68 (FIGS. 17 and 18). During use, when the amplitude is to be changed, the eccentric weight member 54 begins to rotate in the opposite direction from the previous use and the electromagnet 111 is energized, thereby attracting the head portion 116 of the interference member 85 to the deployed position and pulling the stop member 90 away from the movable member and tooth 88, such that stop member 90 is no longer in the linear path of tooth 88 (the tooth path between the first position and the second position) (see FIGS. 19 and 20). As a result, the eccentric or centripetal force causes the movable member 58 to move to the other of the first or second position (from the position in FIG. 25 to the position in FIG. 26 or vice versa). Once this happens or after a predetermined time or when the motor reaches a predetermined RPM, electromagnet 111 is turned off or deenergized and the spring biases the interference member 85 back to the rest position, thereby causing the stop member 90 to move into the linear path of tooth 88 and locking or securing the movable member in either the first or second position (depending on the rotational direction of the eccentric weight member 54).

Figure 24:
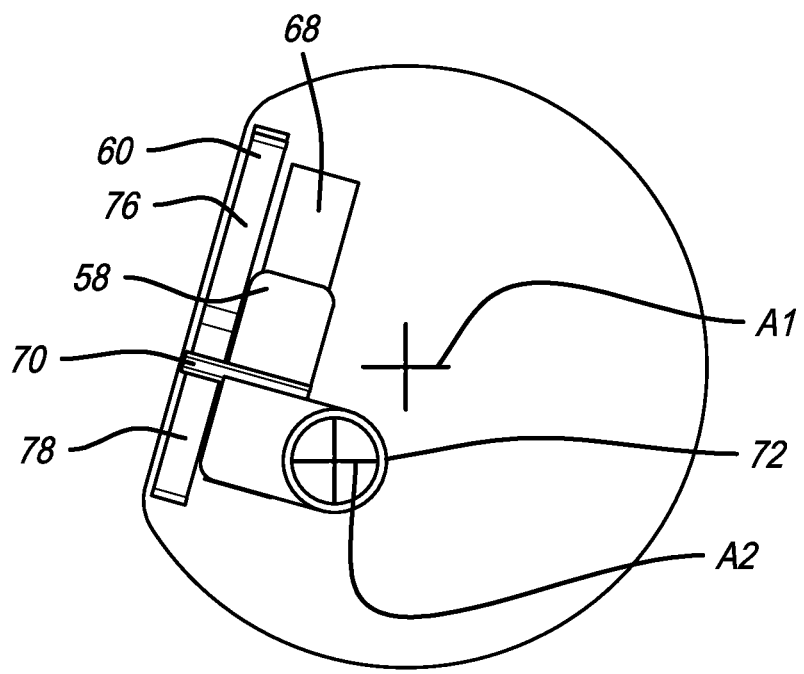
FIG. 24 is an elevational view of the variable amplitude assembly showing the movable member in the second position.

Eccentric force causes the movable member 58 and the slide members 86 to move to the opposite end of the slots 68 when the motor is reversed (and the tooth 88 and stop member 90 are not engaged). It will be appreciated that the movable member 58 will be located at the first position, as shown in FIGS. 17 and 19, when the eccentric weight member 54 is rotated counterclockwise (based on the configuration shown in FIGS. 17-20) and the movable member 58 will be located at the second position, as shown in FIGS. 24 and 26, when the eccentric weight member 54 is rotated clockwise (based on the configuration shown in FIGS. 17-20). Essentially, the opposite ends of slots 68 are stop members that stop the movable member 58 as it moves when the motor direction is reversed. In short, the direction of rotation of the motor drive shaft determines the amplitude of the reciprocating movement of the reciprocating shaft and, therefore, the massage attachment.

FIGS. 17 and 18 also show the axis of rotation A1 of the eccentric weight member 54 and the axis of shaft 72 A2. As can be seen in a comparison of FIG. 17 to FIG. 18, the distance between A1 and A2 is greater when the movable member 58 is in the second position than when the movable member 58 is in the first position. As a result, the reciprocating shaft 20 (and massage attachment 105) have a greater amplitude or stroke when the movable member 58 is in the second position than when the movable member 58 is in the first position. In an exemplary embodiment, the amplitude is 8 mm when the movable member is in the first position (A1 is 4 mm from A2) and 16 mm when the movable member is in the second position (A1 is 8 mm from A2). These numbers are only exemplary and the range can be wider or small than discussed above. In a preferred embodiment, shaft 72 (and A2) are positioned closer to one end of movable member 58 than the other to provide the different distances between A1 and A2 when the movable member is in the first and second positions. It will be appreciated that the drive train can be used with any type of motor. The use of a brushless DC motor is not limiting on the invention.

FIGS. 21-24 show another embodiment of a variable amplitude assembly 52 for use with a drive train in a percussive massage device for varying the amplitude of the output shaft and the massage element or attachment. Variable amplitude assembly 52 operates similarly to other variable amplitude assemblies discussed herein, but uses a leaf spring 60. Therefore, all text herein related to the other embodiments discussed applies to this embodiment as well and all parts are interchangeable.

Figure 21:
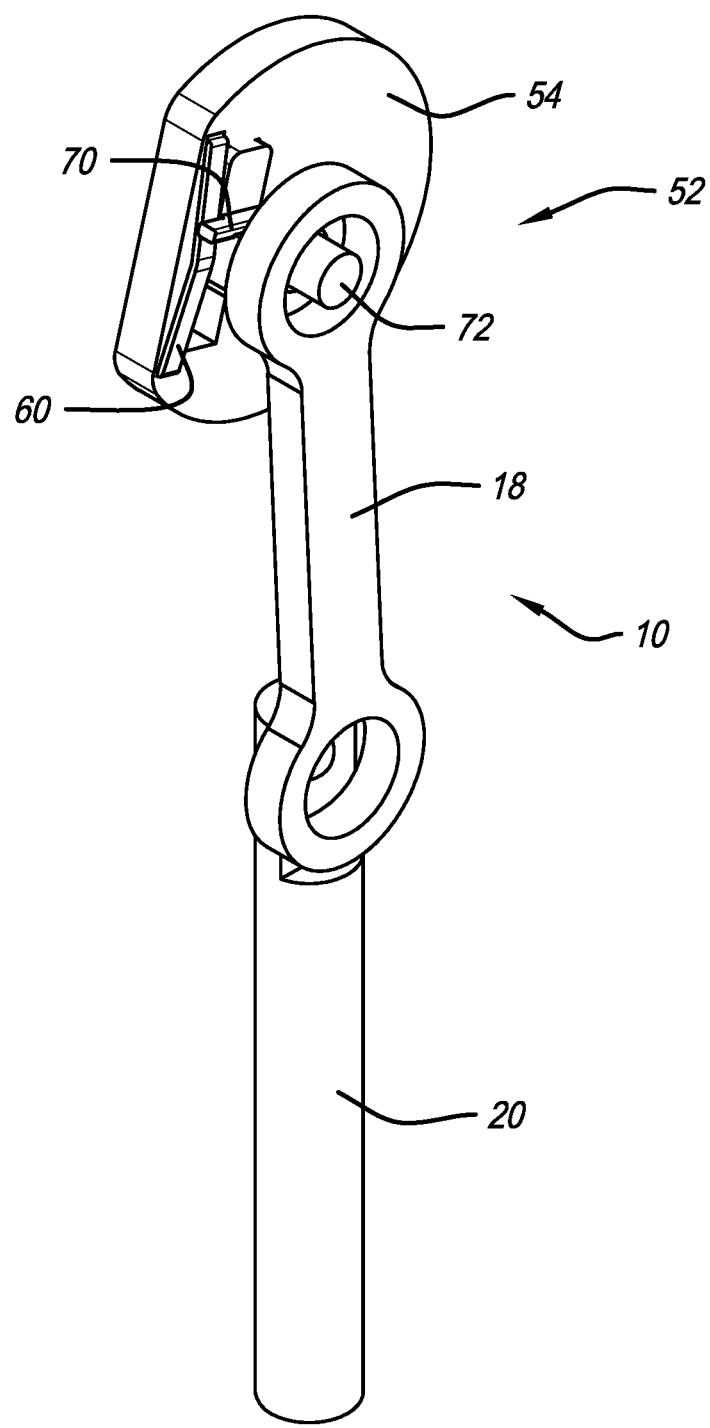
FIG. 21 is a perspective view of a drive train that includes a variable amplitude assembly in accordance with a preferred embodiment of the present invention.
Figure 22:
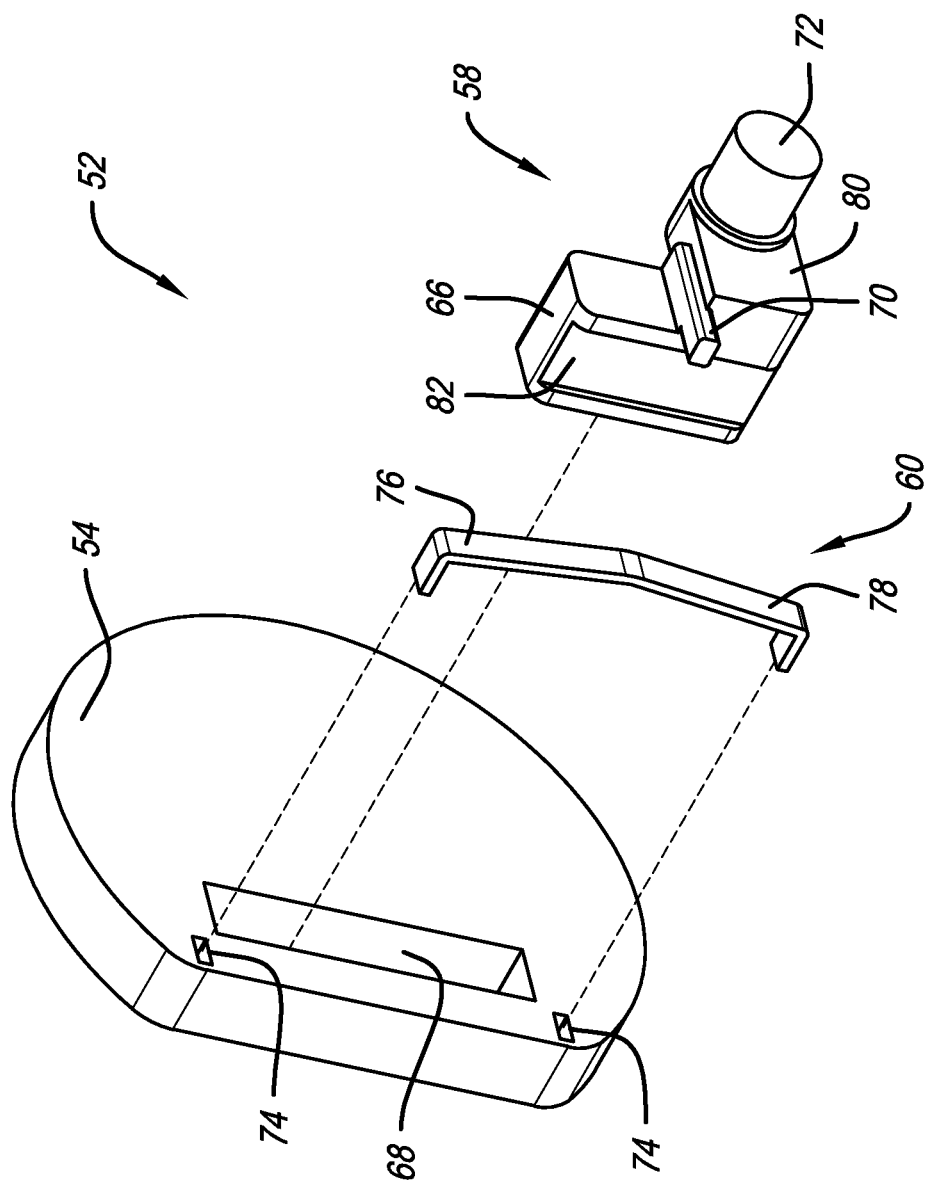
FIG. 22 is an exploded perspective view of the variable amplitude assembly.

As shown in FIGS. 21-22, the variable amplitude assembly 52 includes a eccentric weight member 54, a movable member 58, spring 60 and slot 68. The movable member 58 includes a slide portion 66 that is received in slot 68 that is defined in the eccentric weight member 54, a pin 70 that extends outwardly and contacts spring 60 and an offset shaft 72 that receives and, in use, reciprocates the push rod 18. It will be appreciated that the connections between the push rod 18 and the shaft 72 and the push rod 18 and the reciprocating shaft 20 are not shown in the drawings.

As shown in FIG. 22, the eccentric weight member 54 includes recesses 74 defined therein that receive opposite ends of the spring 60. In a preferred embodiment, the spring 60 is a leaf spring and has a central portion that is spaced from the eccentric weight member 54. The central portion includes a first position portion 76 and a second position portion 78 that meet at an apex. The pin 70 extends outwardly and contacts the first position portion 76 when the movable member 58 is in the first portion and the second position portion 78 when the movable member 58 is in the second portion. The spring 60 is biased away from the eccentric weight member and against the pin 70. As a result, the spring 60 helps hold the movable member 58 in the proper position and also helps prevent rattling and noise. When the rotation of the eccentric weight member 54 is reversed, the eccentric force is enough to overcome the spring force of the spring 60 to allow the movable member 58 to move along slot 68 to the opposite end and for the pin 70 to travel over the apex of the spring 60 and to the other of the first or second position portion.

As shown in FIG. 22, the movable member 58 includes a main body portion 80, the pin 70, the slide portion 66 and shaft 72. In a preferred embodiment, the slide portion 66 also includes channels 82 that engage or slide on the inner surfaces of the long sides of slot 68.

Figure 23:
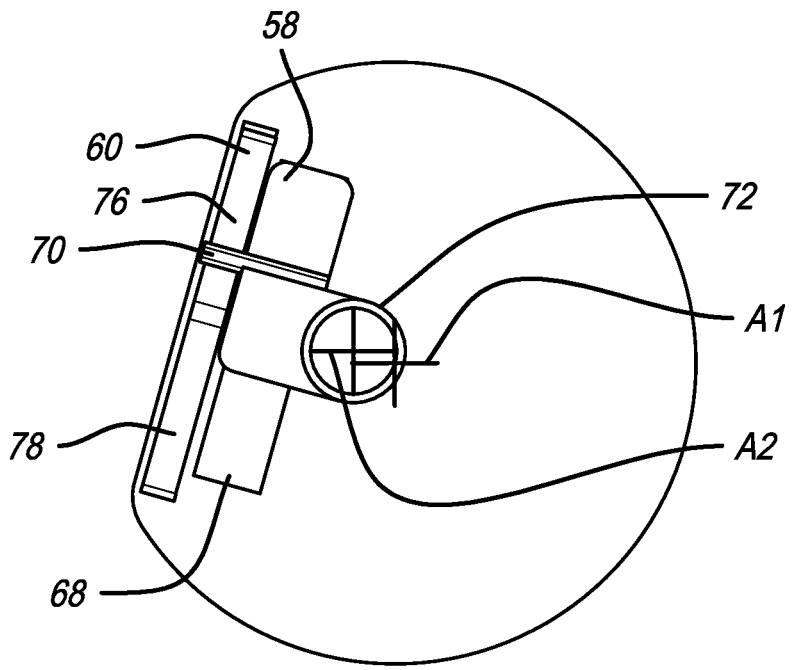
FIG. 23 is an elevational view of the variable amplitude assembly showing the movable member in the first position.

As shown in FIGS. 23 and 24, the movable member 58 is positionable or movable within slot 68 between a first position (FIG. 23) and a second position (FIG. 24). Generally, the movable member 58 is located at the first position when the drive shaft of the motor is rotated in a first direction (clockwise or counterclockwise) and the movable member slides or translates to the second position when the drive shaft is reversed and rotated in the opposite direction. Eccentric force causes the movable member 58 to move to the opposite end of the slot 68 when the motor is reversed. It will be appreciated that the movable member 58 will be located at the first position, as shown in FIG. 23, when the eccentric weight member 54 is rotated clockwise (based on the configuration shown in FIG. 23) and the movable member 58 will be located at the second position, as shown in FIG. 24, when the eccentric weight member 54 is rotated counterclockwise (based on the configuration shown in FIG. 24). Essentially, the opposite ends of slot 68 are stop members that stop the movable member 58 as it moves when the motor direction is reversed. In short, the direction of rotation of the motor drive shaft determines the amplitude of the reciprocating movement of the reciprocating shaft and, therefore, the massage attachment.

FIGS. 23 and 24 also show the axis of rotation A1 of the eccentric weight member 54 and the axis of shaft 72 A2. As can be seen in a comparison of FIG. 23 to FIG. 24, the distance between A1 and A2 is greater when the movable member 58 is in the second position than when the movable member 58 is in the first position. As a result, the reciprocating shaft 20 has a greater amplitude or stroke when the movable member 58 is in the second position than when the movable member 58 is in the first position. In an exemplary embodiment, the amplitude is 8 mm when the movable member is in the first position (A1 is 4 mm from A2) and 16 mm when the movable member is in the second position (A1 is 8 mm from A2). These numbers are only exemplary and the range can be wider or small than discussed above. In a preferred embodiment, slot 68 is angled such that the first position end is closer to the axis of rotation A1 than the second end.

In an exemplary use, the user of the device has the ability to choose the amplitude by pushing a button or otherwise activating a switch. The button or switch can be on the device or can be on a software application "app" executable on an electronic mobile device, such as a phone. After the button is pushed, the selection of the amplitude is processed in the PCB and is translated into a motor shaft rotation direction (e.g., counterclockwise amplitude A, clockwise amplitude B). The motor then begins rotating the shaft and the eccentric weight the appropriate direction, thereby causing the movable member to move to the position to result in the correct amplitude.[1]

[1] Is there more information that can be provided regarding how to activate the amplitude change?

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

Embodiments are envisioned where any of the aspects, features, component or steps herein may be omitted and/or are option. Furthermore, where appropriate any of these optional aspects, features, component or steps discussed herein in relation to one aspect of the invention may be applied to another aspect of the invention.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed, at different times. Further any specific numbers noted herein are only examples: alternative implementations may employ differing values or ranges.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges. It will be appreciated that any dimensions given herein are only exemplary and that none of the dimensions or descriptions are limiting on the present invention.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. § 112, ¶6, other aspects may likewise be embodied as a means-plus-function claim, or in other forms, such as being embodied in a computer-readable medium. (Any claims intended to be treated under 35 U.S.C. § 112, ¶6 will begin with the words "means for"). Accordingly, the applicant reserves the right to add additional claims after filing the application to pursue such additional claim forms for other aspects of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A percussive therapy device comprising:
a housing,
an electrical source,
a motor positioned in the housing,
a switch for activating the motor,
a push rod assembly operatively connected to the motor and configured to provide reciprocating motion in response to activation of the motor,
a variable amplitude assembly that includes a counterweight that is rotatable about a first axis in a first direction and an opposite second direction, and a movable member that is movable with respect to the counterweight between a first position and a second position, wherein the movable member includes an offset shaft extending therefrom that defines a second axis that is parallel to the first axis, wherein the push rod assembly is operatively connected to the offset shaft, wherein the movable member is movable from the first position to the second position when the rotation of the counterweight is reversed from the first direction to the second direction, wherein the second axis is positioned closer to the first axis when the movable member is in the first position than when the movable member is in the second position, wherein the counterweight defines a length that includes a halfway point, and wherein the first axis is offset from the halfway point, and
a massage attachment secured to a distal end of the push rod assembly,
wherein the reciprocating motion of the push rod assembly has a user-adjustable amplitude.

2. The percussive therapy device of claim 1 wherein the distal end of the push rod assembly is configured to reciprocate within a first range, wherein the amplitude is user-adjustable such that the distal end is configured to reciprocate within a second range, and wherein the second range is different than the first range.

3. The percussive therapy device of claim 2 further comprising an input that changes the amplitude from the first range to the second range.

4. The percussive therapy device of claim 2 wherein the motor is configured to rotate the counterweight about the first axis in a first direction and an opposite second direction, wherein when the counterweight is rotated in the first direction the distal end of the push rod assembly reciprocates within the first range, and wherein when the counterweight is rotated in the second direction the distal end of the push rod assembly reciprocates within the second range.

5. The percussive therapy device of claim 4 wherein the distal end of the push rod assembly reciprocates within the first range when the movable member is in the first position, wherein the distal end of the push rod assembly reciprocates within the second range when the movable member is in the second position, and wherein the movable member is movable from the first position to the second position when the rotation of the counterweight is reversed from the first direction to the second direction.

6. The percussive therapy device of claim 5 wherein a slot is defined in the counterweight, wherein the movable member includes a main body portion with a slide member extending therefrom, wherein the slide member is received in and movable within the slot.

7. The percussive therapy device of claim 5 wherein the variable amplitude assembly includes an interference member that is positioned in a channel defined in the counterweight, wherein the interference member is movable between a deployed position and a rest position, wherein in one of the deployed position or the rest position the interference member prevents the movable member from moving between the first position and the second position, and wherein in the other of the deployed position and the rest position the interference member does not prevent the movable member from moving between the first position and the second position.

8. The percussive therapy device of claim 7 wherein in the deployed position the interference member prevents the movable member from moving between the first position and the second position, and wherein in the rest position the interference member does not prevent the movable member from moving between the first position and the second position, wherein the interference member is biased to the rest position by a spring.

9. The percussive therapy device of claim 8 wherein the interference member is movable from the rest position to the deployed position when the counterweight rotates at a predetermined RPM.

10. The percussive therapy device of claim 8 wherein the interference member includes a stop member, wherein the movable member includes a tooth, and wherein in the deployed position the stop member blocks the tooth to prevent the movable member from moving between the first position and the second position.

11. A variable amplitude assembly comprising:
a counterweight that is rotatable about a first axis in a first direction and an opposite second direction,
a movable member that is movable with respect to the counterweight between a first position and a second position, wherein the movable member includes an offset shaft extending therefrom that defines a second axis that is parallel to the first axis, wherein the movable member is movable from the first position to the second position when the rotation of the counterweight is reversed from the first direction to the second direction, wherein the second axis is positioned closer to the first axis when the movable member is in the first position than when the movable member is in the second position, and wherein the counterweight defines a length that includes a halfway point, and wherein the first axis is offset from the halfway point.

12. The variable amplitude assembly of claim 11 wherein a slot is defined in the counterweight, wherein the movable member includes a main body portion with a slide member extending therefrom, wherein the slide member is received in and movable within the slot.

13. The variable amplitude assembly of claim 11 further comprising an interference member that is positioned in a channel defined in the counterweight, wherein the interference member is movable between a deployed position and a rest position, wherein in one of the deployed position or the rest position the interference member prevents the movable member from moving between the first position and the second position, and wherein in the other of the deployed position and the rest position the interference member does not prevent the movable member from moving between the first position and the second position.

14. The variable amplitude assembly of claim 13 wherein in the deployed position the interference member prevents the movable member from moving between the first position and the second position, and wherein in the rest position the interference member does not prevent the movable member from moving between the first position and the second position, wherein the interference member is biased to the rest position by a spring.

15. The variable amplitude assembly of claim 14 wherein the interference member is movable from the rest position to the deployed position when the counterweight rotates at a predetermined RPM.

16. The variable amplitude assembly of claim 14 wherein the interference member includes a stop member, wherein the movable member includes a tooth, and wherein in the deployed position the stop member blocks the tooth to prevent the movable member from moving between the first position and the second position.

17. The variable amplitude assembly of claim 14 wherein the spring extends through an opening defined in the interference member.

18. The variable amplitude assembly of claim 13 wherein the interference member is moveable linearly within the channel in a first direction between the deployed position and the rest position, wherein the movable member is moveable linearly with respect to the counterweight in a second direction between the first position and the second position, and wherein the first direction is perpendicular to the second direction.

19. A variable amplitude assembly comprising:
a counterweight that is rotatable about a first axis in a first direction and an opposite second direction,
a movable member that is movable with respect to the counterweight between a first position and a second position, wherein the movable member includes an offset shaft extending therefrom that defines a second axis, wherein the movable member is movable from the first position to the second position when the rotation of the counterweight is reversed from the first direction to the second direction, and wherein the second axis is positioned closer to the first axis when the movable member is in the first position than when the movable member is in the second position, and
an interference member that is positioned in a channel defined in the counterweight, wherein the interference member is movable between a deployed position and a rest position, wherein in one of the deployed position or the rest position the interference member prevents the movable member from moving between the first position and the second position, and wherein in the other of the deployed position and the rest position the interference member does not prevent the movable member from moving between the first position and the second position, and wherein the interference member is configured to move independently from the movable member.

* * * * *